(12) United States Patent
Casse et al.

(10) Patent No.: US 10,449,382 B2
(45) Date of Patent: Oct. 22, 2019

(54) IMPLANTABLE NEURAL MODULATION DEVICE

(71) Applicant: Palo Alto Research Center Incorporated, Palo Alto, CA (US)

(72) Inventors: Bernard D. Casse, Saratoga, CA (US); George Daniel, Palo Alto, CA (US); Jonathan Rivnay, San Francisco, CA (US); Christopher Paulson, Livermore, CA (US); Robert Street, Palo Alto, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 344 days.

(21) Appl. No.: 15/616,479

(22) Filed: Jun. 7, 2017

(65) Prior Publication Data

US 2018/0353283 A1   Dec. 13, 2018

(51) Int. Cl.
*A61N 2/02* (2006.01)
*A61N 2/00* (2006.01)

(52) U.S. Cl.
CPC .............. *A61N 2/006* (2013.01); *A61N 2/02* (2013.01); *A61F 2250/0096* (2013.01)

(58) Field of Classification Search
CPC .............. A61N 2/006; A61N 2/02; A61F 2/14
See application file for complete search history.

(56) References Cited

U.S. PATENT DOCUMENTS

| 5,314,495 | A | * | 5/1994 | Kovacs | A61B 17/1128 607/48 |
|---|---|---|---|---|---|
| 10,328,255 | B2 | * | 6/2019 | Rapoport | A61N 1/0534 |
| 2005/0234286 | A1 | * | 10/2005 | Riehl | A61N 2/006 600/9 |
| 2012/0323288 | A1 | * | 12/2012 | Anderson | A61N 1/0531 607/3 |
| 2017/0232267 | A1 | * | 8/2017 | Riehl | A61N 2/006 600/13 |

OTHER PUBLICATIONS

Coulombe et al., "A Highly Flexible System for Microstimulation of the Visual Cortex: Design and Implementation", IEEE Transactions on Biomedical Circuits and Systems, vol. 1, No. 4, Dec. 2007, pp. 258-269.
Grimm et al., "Rolled-up nanomembranes as compact 3D architectures for field effect transistors and fluidic sensing applications", Nano Letters, vol. 12, No. 1, 2013, pp. 213-218.
(Continued)

*Primary Examiner* — Christine H Matthews
(74) *Attorney, Agent, or Firm* — Hollingsworth Davis, LLC

(57) ABSTRACT

An implantable subsystem includes multiple implantable neural probes disposed on a flexible substrate. Each neural probe is configured to magnetically stimulate brain neurons. Each probe includes an array of magnetic neural stimulators that magnetically stimulate neurons. Each probe also includes neural probe activation circuitry comprising thin film switches disposed on the flexible substrate. The thin film switches are electrically coupled to row and column activation lines and selectively activate the magnetic neural stimulators in response to neural stimulation activation signals carried on the activation lines.

20 Claims, 33 Drawing Sheets

(56) References Cited

OTHER PUBLICATIONS

Karnaushenko et al., "Compact helical antenna for smart implant applications", NPG Asia Materials, vol. 7, 2015, 10 pages.
Lewis et al., "Restoration of vision in blind individuals using bionic devices: A review with a focus and cortical visual prostheses", Brain Research 1595, 2015, pp. 51-73.
Luchnikov et al., "Self-Rolled Polymer and Composite Polymer/ Metal Micro- and Nanotubes with Patterned Inner Walls", Adv. Mater. vol. 17, 2005, pp. 1177-1182.
Macabee et al., "Magnetic Coil Stimulation of Straight and Bent Amphibian and Mammalian Peripheral Nerve In Vitro: Locus of Excitiation", Journal of Physiology, 460, 1993, pp. 201-219.
Piedade et al., "Visual Cortical Neuroprosthesis: A System Approach", 2008, 36 pages.
Wang et al., "Characteristics of electrode impedance and stimulation efficacy of a chronic cortical implant using novel annulus electrodes in rat motor cortex", Journal of Neural Engineering, vol. 10, No. 4, Jul. 3, 2013.

\* cited by examiner

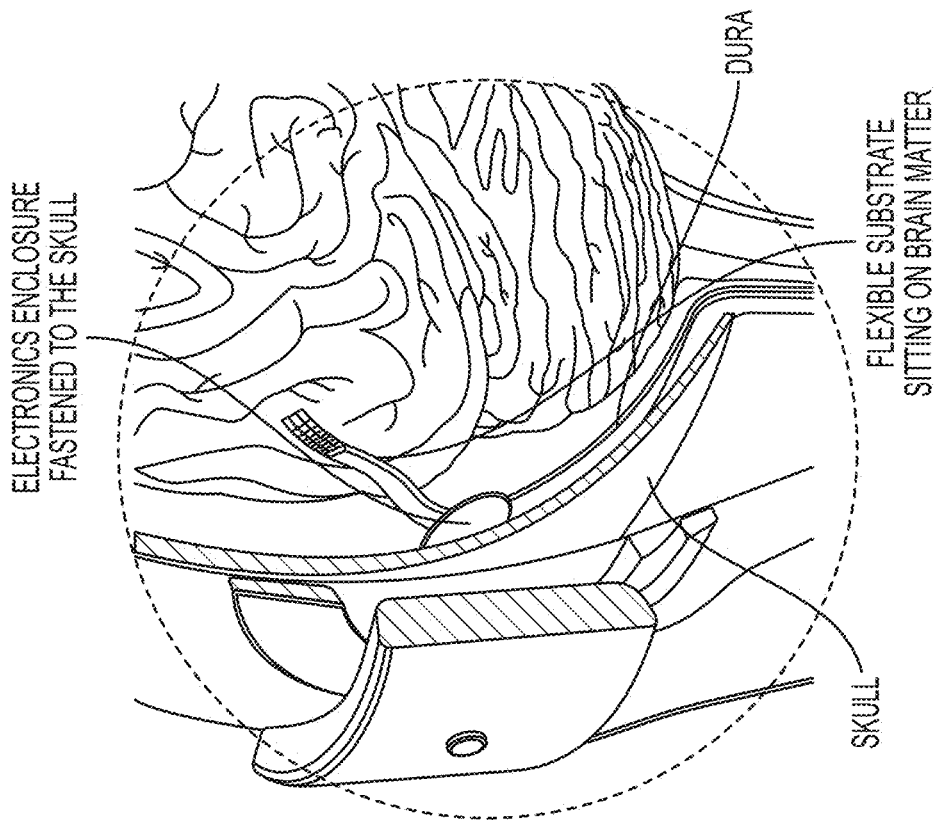
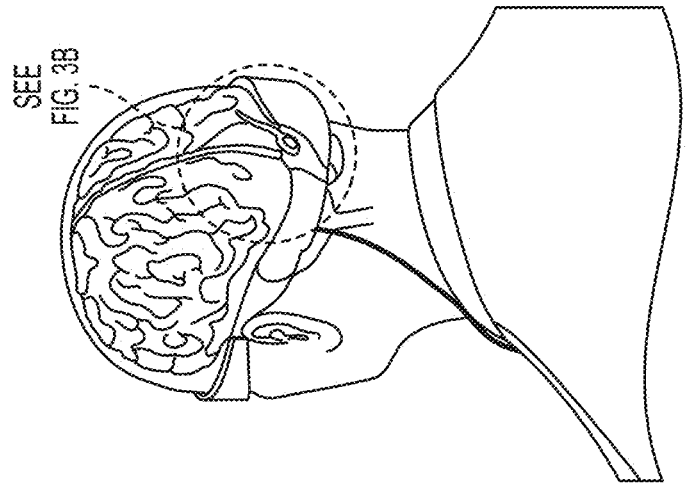
FIG. 3B
FIG. 3A

IMPLANTABLE NEURAL MODULATION DEVICE

RELATED PATENT DOCUMENTS

This patent application is related to U.S. Publication No. 2018-0353766, having the title "IMPLANTABLE NEURAL PROBE," U.S. Publication No. 2013-0353284, having the title "NEURAL MODULATION SYSTEM," both of which are incorporated herein by reference.

TECHNICAL FIELD

This disclosure relates generally to an implantable neural modulation device and to methods and systems related to an implantable neural modulation device.

BACKGROUND

Neural modulation can be used in prostheses to compensate for reduced function. For example, visual prosthetics that use neural modulation can improve visual acuity for many of the approximately 285 million people worldwide who are visually impaired.

SUMMARY

Some embodiments are directed to an implantable subsystem. The subsystem includes multiple implantable neural probes disposed on a flexible substrate. Each neural probe is configured to magnetically stimulate brain neurons. Each probe includes an array of magnetic neural stimulators configured to magnetically stimulate neurons. Each probe also includes neural probe activation circuitry comprising thin film switches disposed on the flexible substrate. The thin film switches are electrically coupled to row and column activation lines and selectively activate the magnetic neural stimulators in response to neural stimulation activation signals carried on the activation lines.

Some embodiments involve an implantable subsystem that includes a flexible substrate having a first surface and a second surface, the flexible substrate having a distal section, a proximal section, and a center section extending between the distal section and the proximal section. A two dimensional array of neural probes that stimulate and sense neurons is disposed at the distal section of the flexible substrate. Each neural probe includes a probe area of the flexible substrate that has a three dimensional shape with an external surface comprising at least a portion of the first surface of the flexible substrate and an internal surface comprising at least a portion of the second surface of the probe. Each proble includes an array of magnetic neural stimulators configured to magnetically stimulate neurons and an array of neural sensors disposed on the exterior surface of the probe and configured to electrically sense the neurons. Probe addressing circuitry disposed on the interior surface of the probe includes thin film switches selectively activates the magnetic neural stimulators and the neural sensors. An interface region is disposed at the proximal section of the flexible substrate and is configured to electrically and mechanically couple to an implantable device that controls operation of the neural probes via the probe addressing circuitry.

BRIEF DESCRIPTION OF THE DRAWINGS

FIGS. 3A and 3B respectively show portions of the patient-external device, the patient-internal device, and the flexible membrane with neural probes contacting the visual cortex in accordance with some embodiments;

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Embodiments disclosed herein are directed to a neural prosthetic system and to related devices and methods. According to some embodiments, the prosthetic system magnetically stimulates neurons within the brain to restore body functionality. In the illustrated example, a visual prosthetic system magnetically stimulates neurons within the visual cortex to simulate sight for visually impared people. Neural activation signals produced in response to the magnetic neural stimulation are sensed and the sensed neural activation is used to adapt the magnetic stimulation to achieve the desired visual functionality. Although the example of a visual prosthetic are described herein, it will be appreciated that other applications involving brain stimulation are also possible using the systems, devices, and methods discussed herein.

Figure 1A:
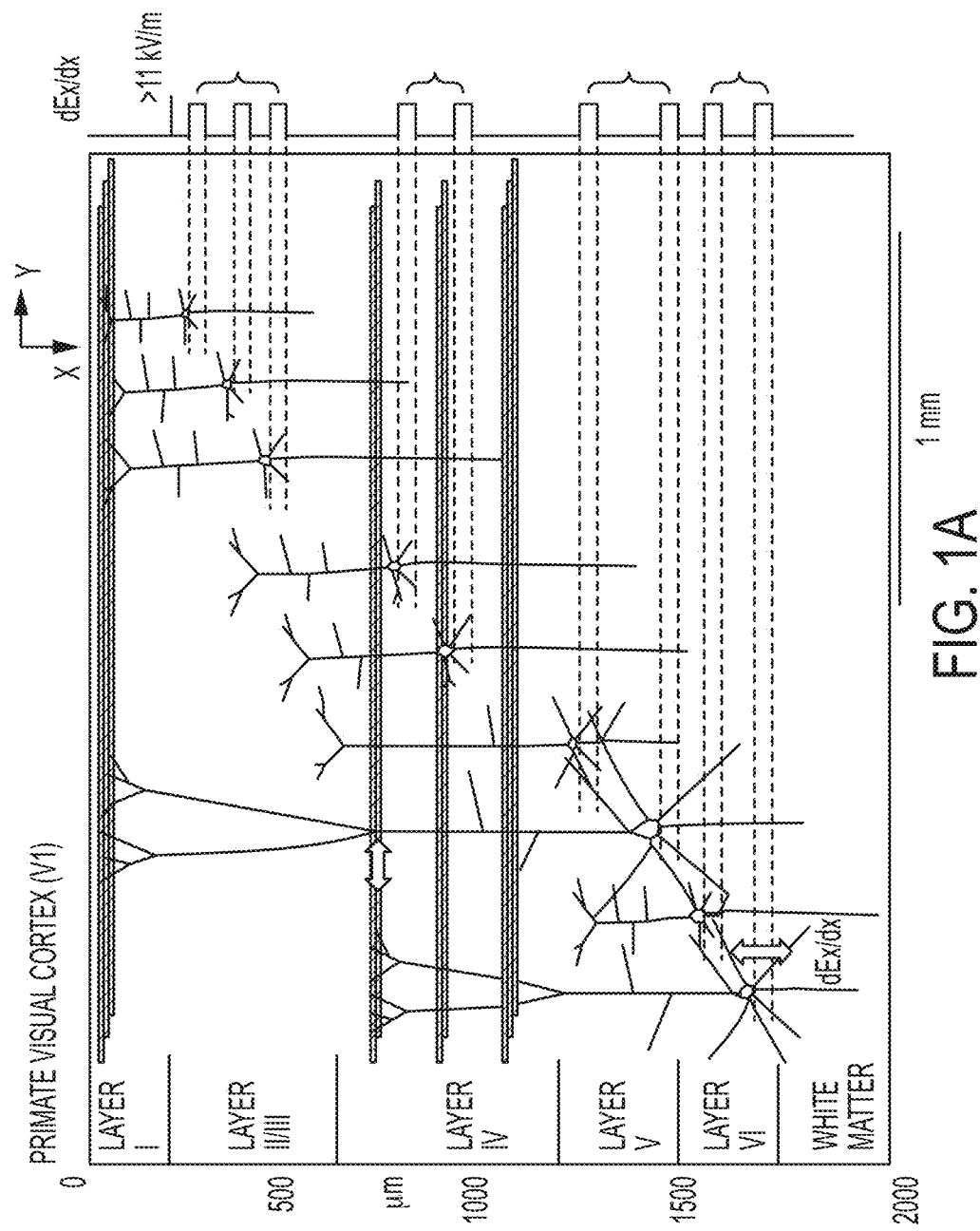
FIG. 1A is a diagram that illustrates intracortical layers.

The therapeutic goal of the visual prosthetic system is to restore at least some level of vision to the blind, particularly those who have suffered trauma of the eye or diseases such as glaucoma, macular degeneration, and retinitis pigmentosa —by implanting a prosthetic into the primary visual cortex (V1) of blind subjects. The intracortical layers of the primate visual cortex are illustrated in FIG. 1A. Prostheses that target the retina or other early visual centers can treat only a few forms of blindness. However, a system as discussed herein that targets the cortex is useful for a much wider range of visual deficits, up to and including traumatic loss of the eye.

According to some embodiments, the visual prosthetic system discussed herein can target about 100,000 distinct visual neurons. Tiny, spatially asymmetric magnetic fields can be scaled to activate only single neurons, or to activate larger populations in the immediate surroundings of each coil. The asymmetric fields have a strong component oriented perpendicularly to the cortical surface and a much weaker component that is parallel.

The approach discussed herein involves the consideration that perpendicularly-oriented pyramidal neurons can be activated while axons of passage and other horizontally-oriented processes will not. Pyramidal neurons are an attractive target because they are the major excitatory neurons of the cortex and their output serves as the primary communication signal with all other regions of the cortex, as well as other brain centers. Avoiding the axons of passage and other horizontal processes further ensures that activation remains confined to narrow regions around each coil, instead of the unwanted spread of activation that arises from the indiscriminate activation of axons that occurs with electrodes. The high permeability of magnetic fields offers increased reliability over other devices (i.e., coils are not susceptible to encapsulation or other biological responses to implantation).

It can be desirable for the prosthetic system to replicate key elements of physiological signaling. Each probe (the part of the prosthetic inserted into the cortex) can be capable of selectively activating the pyramidal neurons of individual cortical layers, (e.g., 2,3, 5 and 6 as well as the granule cells of layer 4). The granule cells are the input neurons of the cortex and their activation will in turn utilize the downstream synaptic circuitry. This will result in closer matches to physiological signaling in each type of (downstream) pyramidal cell. However, even with the high level of selectivity that can be achieved with micro-coils, the neural patterns that arise in each type of pyramidal neuron are not likely to perfectly match physiological patterns. Thus, the ability to independently activate each type of pyramidal neuron can be used to bring the resulting neural signal (in each PN) more in line with its normal physiological response. While perfect matches to physiological signaling may not be possible, the ability to match certain important elements of such signaling is likely to greatly improve the quality of elicited vision.

In addition to the ability of the prosthetic system to stimulate up to 100,000 or more neurons independently, the system may also record from (sense) at least 1 million cortical neurons. Implanted tetrodes can capture signals from thousands of neurons simultaneously, thereby greatly reducing the number of penetrations by the probes that need to be made into the cortex. The ability to simultaneously read and write neural activity offers tremendous opportunities for unraveling key elements of cortical function, but will also be highly useful for improving the efficacy of the prosthetic. The ability to read the neuronal responses that arise in response to stimulation will provide feedback on the level of similarity between induced and physiological patterns, and lead to enhanced stimulation strategies that produce matches that are within specified design parameters.

Simultaneous stimulation and recording with the same device poses a considerable challenge because the electrical artifacts induced by the stimulus waveform can complicate the elicited neural response. Fortunately, the tiny magnetic fields that arise from the magnetic coils produce very small artifacts that do not significantly impede the ability to detect spikes. For this application, the design criteria for a neural implant in accordance with some embodiments is summarized below.

Figure 1B:
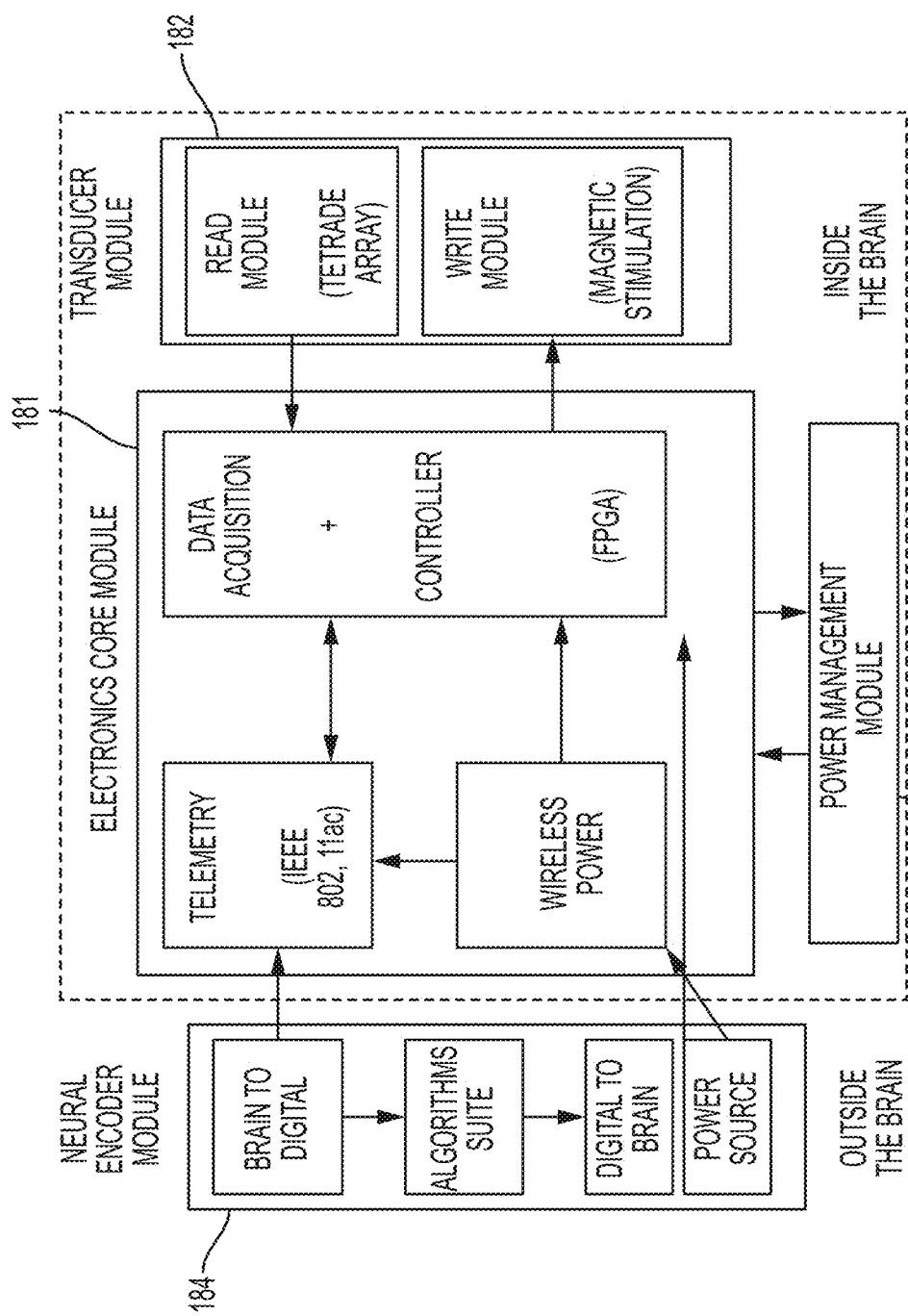
FIG. 1B shows functional system components of the vision prosthetic system in accordance with some embodiments.

FIG. 1B shows functional system components of the vision prosthetic system in accordance with some embodiments. The functional components are grouped into four modules: the core electronics module 181, the transducer module 182, the power management module 183, and the neural encoder module 184. The neural encoder module 184 resides outside the brain, and be disposed on a headband head band, its main role being to provide the more intensive (and heat generating) signal processing computations.

The neural encoder module 184 is programmed to map camera signals responsive to an image to neural stimulation signals that will cause the patient to "see" the image. The neural encoder module includes a brain to digital component that receives information from neural sensor signals and a digital to brain component that sends pattern information for the neural stimulation to the internal electronics core module. The algorithms suite maps the camera signals to the neural stimulation pattern.

The transducer module 182, which is physically wired to the core electronics module 181, contains the tetrode array and micro-coils on a common substrate for reading and writing to neurons, respectively. The electronics module 181 is responsible for current injection in the micro-coils, acquisition of data from the read submodule, telemetry, and distribution of power to the sub-modules. The electronics module 181 can be wirelessly powered from a head band. To ensure that the implanted device stays within thermal safety limits, the system includes a power management module 183.

The transducer module 182 comprises a flexible substrate comprising an array of probes, e.g. cylindrical probes, as described in greater detail herein. The probes include tetrodes for sensing neural activity and micro-coils for stimulating neurons. In some embodiments, the surface of the probe consists of alternating structures of tetrode (sensing) and micro-coil (stimulating) structures.

The prosthetic systems illustrated herein provide an adaptive neural transducer technology platform for high density operations that read neural signals and/or stimulate neurons. Systems described herein are capable of real-time data processing and dynamic control of brain functions. The cortical-based visual prosthetic provides a representative therapeutic application. In some embodiments, the visual prosthetic can sense at least $10^6$ neurons and can stimulate at least $10^5$ neurons, although other numbers of neurons sensed and/or stimulated are also possible. According to some embodiments, intracortical layers 2,3, and 5,6 may be stimulated, the cortical area stimulated can be between about 1.5 to about 2.5 cm$^2$, e.g., about 2 cm$^2$, with a resolution of between about 15 to about 25 µm, e.g., 20 µm in some embodiments. In some embodiments, vertically oriented neurons (VONs) may be selectively stimulated. The prosthetic is capable of generating patterns of neural activity leading to predictable visual perception in primates. The visual prosthetic system described herein is configured to 1) implement safe, long-term, high-density, and high-selectivity sense/stimulation interfaces, 2) process hierarchical data at scale and in real-time, and 3) adaptively interact with cortical function.

Previous neural interfaces using in human clinical studies were largely based on electrical sensing (also referred to as "recording") and electrical stimulation. For neural sensing, localized, multi-shank probes allow for simultaneous sensing of closely spaced neuron populations and for the determination of the spatial relationships among isolated single neurons. Embodiments described herein include implementation of electrical sensing which causes reduced or minimal damage to cortical structures.

Whereas electrical neural sensing is useful, neural stimulation by electrical signals is suboptimal. Electrical stimulation is not selective, damages tissue, and is known to trigger immune responses. To overcome these limitations, the visual prosthetic disclosed herein employs a magnetic stimulation approach based on micro-coils. Magnetic stimulation offers enhancements over electrical stimulation in that it is highly selective, is able to penetrate biological tissues (e.g., is not impacted by biological encapsulation), has constant stimulation efficacy over time, and is a contactless and safe method. In general, the coils may have any suitable geometry, e.g., planar or non-planar coils. In the disclosed embodiments, a three dimensional (3D) micro-coil geometry allows reduced current injection when compared to a planar coil. For example, the current injection of the 3D micro-coil may be reduced about 100 times when compared to the planar coil, reducing the total power dissipation of 100 k coils from 1 Watt to less than about 10 mW. In addition, 3D micro-coils provide more degrees of freedom to create spatially-asymmetric fields, and to confine activation to highly focused regions when compared to flat magnetic coils and/or electrical stimulation approaches. The 3D micro-coils can be used to implement a field manipulation method involving focused magnetic field (FMS), that enables more localized stimulations, better depth control, and complex stimulation patterns (via beam shaping and beam steering) when compared to flat magnetic coils and/or electrical stimulation approaches. For example, in some implementations an array of 3D micro-coils may be designed to have a sub-neuronal resolution of less than about 25 µm.

Embodiments of the visual prosthetic disclosed herein uses a flexible electronics backplane with thin film transistors (TFTs) switches that support massive multiplexing of the neural sensed signals and neural stimulation signals. In these embodiments, the role of the flexible electronics platform is two-fold: it minimizes tissue damage through better mechanical flexibility, and provides multiplexing at the neural sense and/or stimulation sites. The use of TFTs for multiplexing can reduce the number data lines that must be routed upstream to detection electronics to a few hundred of data lines. The TFTs also allow lower-level logic circuitry to be disposed locally on the neural probes that include the neural sensors and neural stimulators.

Sensing and/or stimulating neurons using dense array of sensing or stimulation transducers can be challenging. Power and heat constraints are involved for such intensive on-board computation. To address these challenges, the electronics and algorithms of the visual prosthetic system disclosed herein are partitioned between an implanted device and a patient-external wearable device that is wirelessly communicatively coupled to the implanted device. Compression algorithms enable transmission of data between the implanted and external devices via the bandwidth-limited wireless telemetry. The distribution of the electronics and algorithms between the implanted device and the external device enhances accuracy while reducing on-board power use and heat generation of the implanted device.

The algorithms initially used for stimulating the neurons can be derived by high frequency sampling of neural signals produced by non-human primates with intact vision pathways at the intended stimulation areas an optionally areas farther down the vision pathway. The stimulating algorithms initially developed from the neural signals in non-human primates that are not blind can be subsequently refined for the patient using the visual prosthesis system using machine learning based on feedback signals from the patient's neural sensors. The machine learning is implemented until the stimulation produces the desired neural signals and the algorithm is updated accordingly.

Figure 1C:
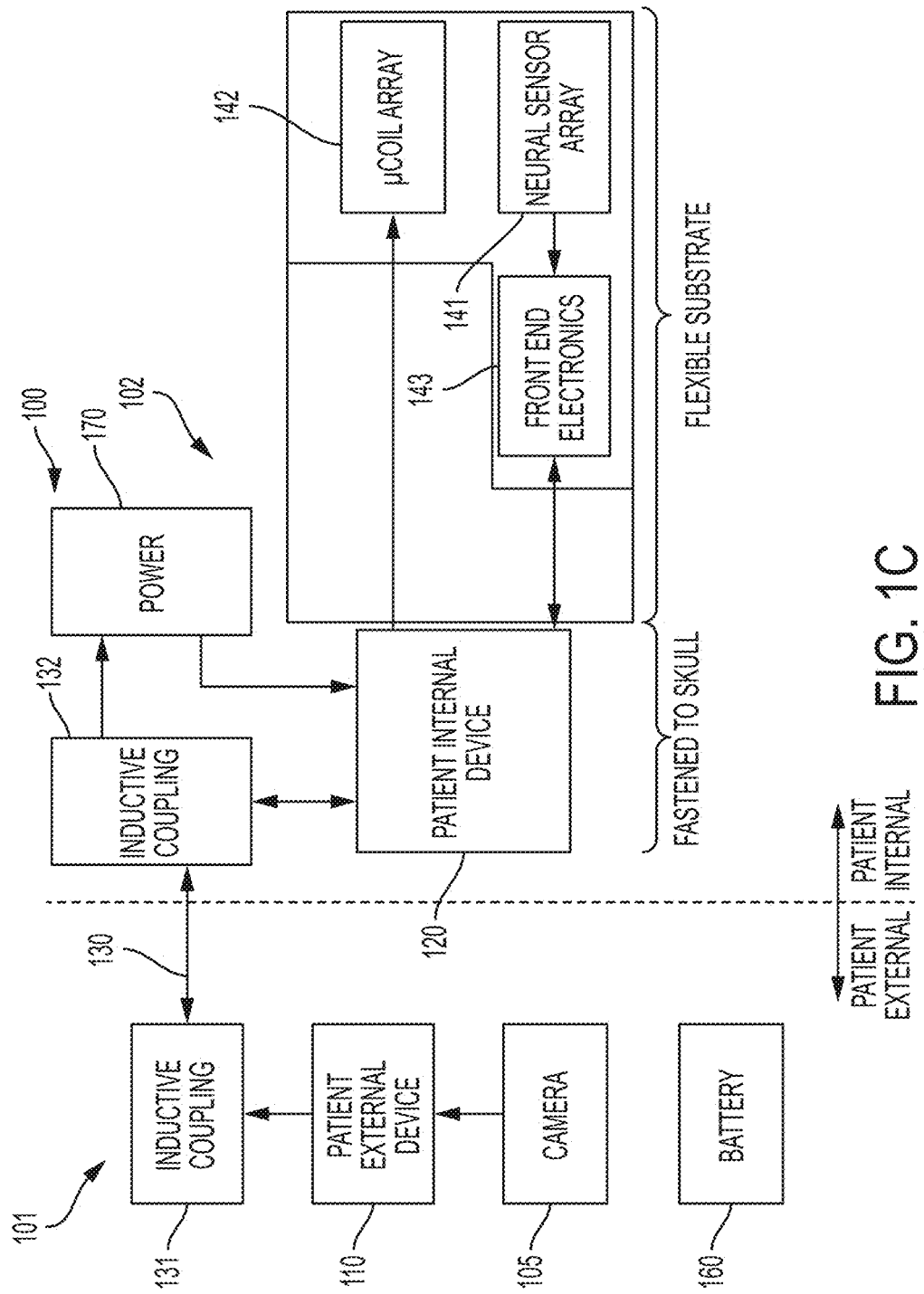
FIG. 1C is a block diagram of a visual prosthetic system in accordance with some embodiments.

Turning now to FIG. 1C, there is shown a block diagram of a cortical-based visual prosthetic system 100 in accordance with some embodiments. As previously discussed, the visual prosthetic system 100 may have the capability of stimulating (writing to) at least $10^5$ neurons and sensing (reading) at least $10^6$ neurons. The visual prosthetic system 100 includes a patient-external first portion 101 disposed outside the patient's body and a patient-internal first portion 102 configured to be implanted within the skull of the patient. The patient-external portion 101 includes a camera 105 and a patient-external electronic device 110. The patient-internal portion 102 includes a patent-internal device 120 coupled to a flexible substrate 150 that supports addressing circuitry and an array of neural probes 140.

Image signals from the camera 105, which may be mounted on glasses or goggles, are transferred to patient-external control electronics 110. The image signals are processed according to a vision algorithm implemented by the patient-external electronic device 110 and/or the patient-internal electronic device 120. The patient-external and patient-internal electronic devices 110, 120 are communicatively coupled through a wireless communication channel 130 formed by internal and external electromagnetic coupling circuitry 131, 132. The vision algorithm converts the image signals of the camera 105 into neural stimulation control signals for controlling the stimulation micro-coils of the neural probes.

The patient-internal electronic device 120 includes electronic circuitry disposed within a suitable biocompatible housing that is fastened to the interior surface of the patient's skull. The patient-internal device 120 is coupled through the flexible membrane 150 to the neural probes 140 which can be positioned to directly contact the visual cortex. The neural probes 140 may include at least one sensor array 141 configured to sense neural activity of the visual cortex and at least one stimulation micro-coil 142 array configured to stimulate the visual cortex. The flexible, biocompatible membrane 150 supports address lines that select neural sensors and stimulators and data lines that carry the sensor and stimulation signals. The flexible substrate 150 may support TFTs and/or other circuitry that provide for addressing the sensors 141 and micro-coils 142 and carrying the sensor and stimulation signals from the internal device 120 to the sensors 141 and micro-coils 142.

The electronics of the patient-external device 110 and the camera 105 are powered by a portable battery 160. The electronics of the patient-internal device 120 and addressing electronics 143 (e.g., TFTs and related circuitry) of the neural probe 140 are powered by inductive energy transmitted from the patient-external inductive transmitting coil 131 to the implanted inductive receiving coil 132. The current produced in the inductive coil 132 by the transmitted inductive energy is rectified and regulated in the power component 170 of the patient-internal device 120. The power component 170 supplies power to the patient-internal device 120, front end electronics 143, and probes 140.

Figure 2A:
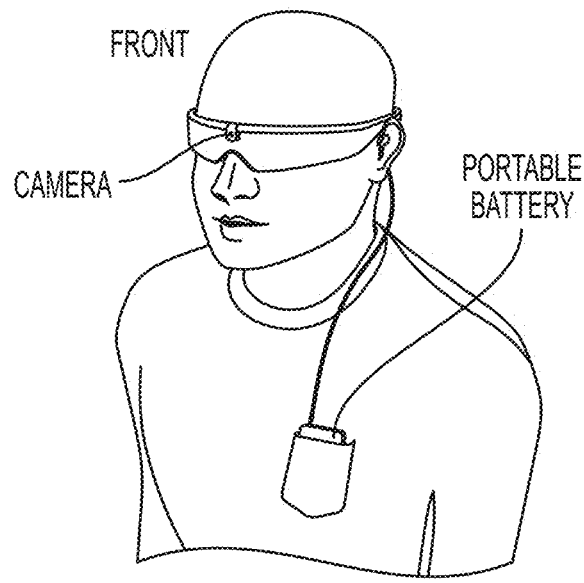
FIGS. 2A and 2B respectively provide front and back views of a person wearing the visual prosthetic system in accordance with some embodiments.
Figure 2B:
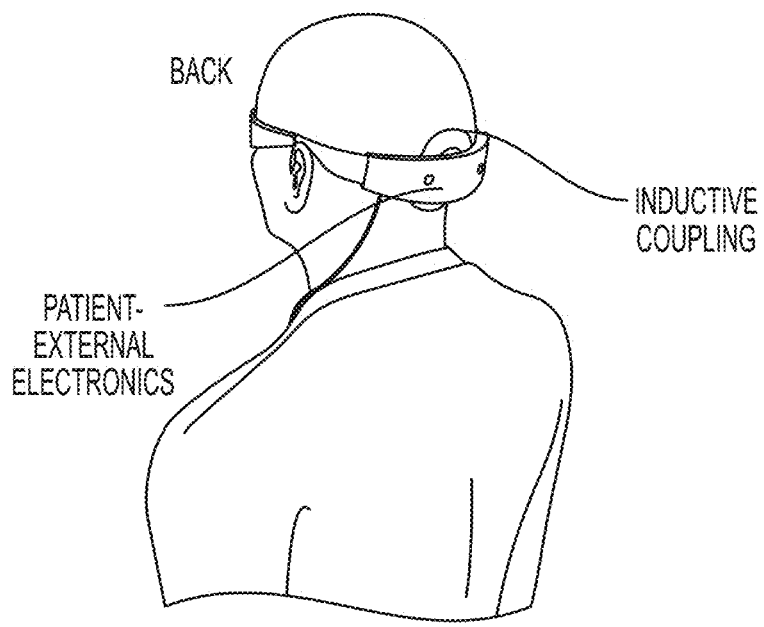

FIGS. 2A and 2B respectively provide front and back views of a person wearing the visual prosthetic system 100. FIGS. 3A and 3B respectively show portions of the patient-external device 110, the patient-internal device 120, and the flexible membrane 150 with neural probes 140 contacting the visual cortex.

Figure 4:
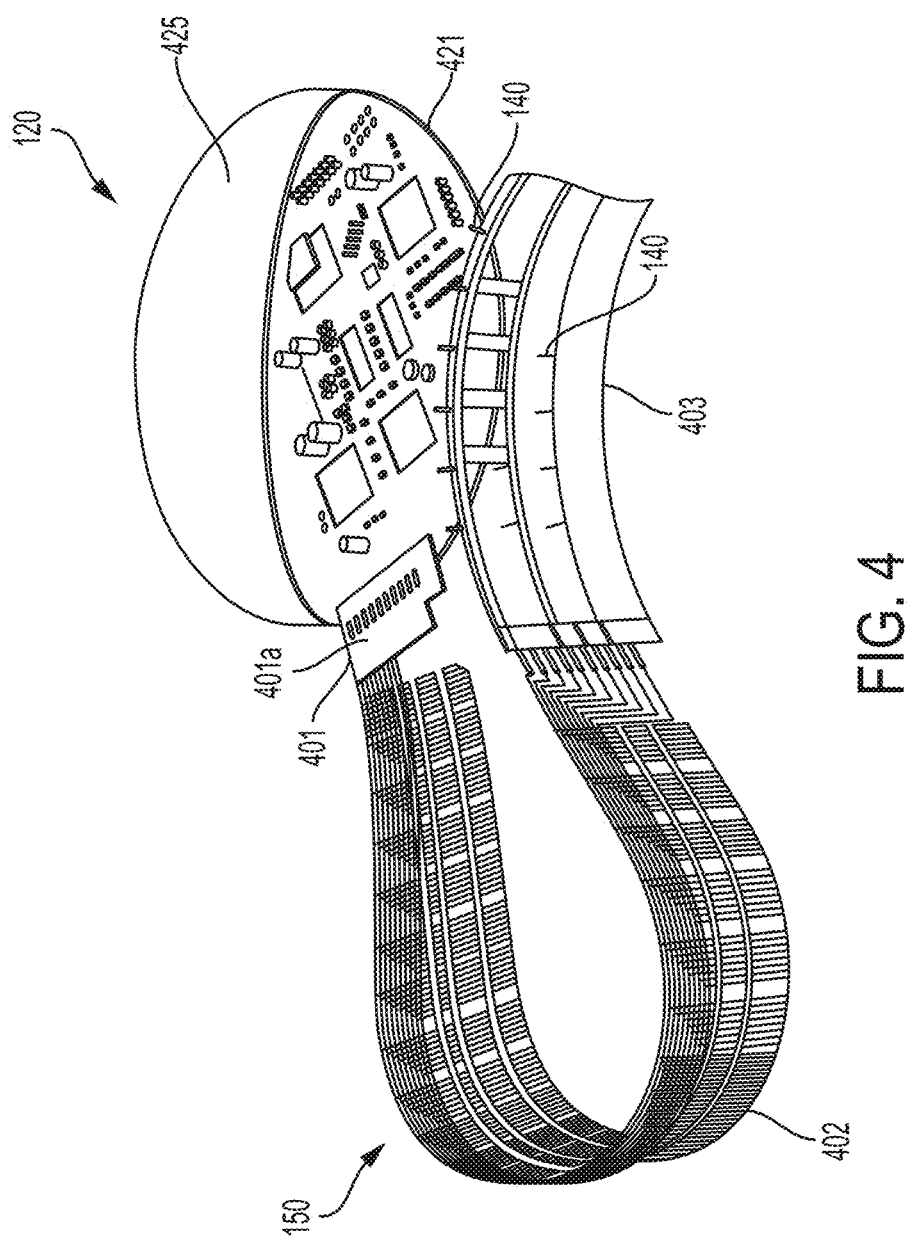
FIG. 4 shows in more detail the patient-internal device of the visual prosthetic system in accordance with some embodiments.

FIG. 4 shows in more detail the patient-internal device 120 of the visual prosthetic system 100. The patient-internal device 120 includes electronics 421 contained within an enclosure 425 having a volume of less than about 1 cm$^3$ in some embodiments. In some configurations, the enclosure 425 may have a volume in a range of about 2 cm$^3$ to about 0.5 cm$^3$. For example, the volume of the enclosure 425 may be less than about 1 cm$^3$ in some embodiments. The enclosure 425 containing the electronics 120, flexible membrane 150, and neural probes 140 are configured to be implanted within the skull of the patient and are made of suitable materials for implantation. The flexible substrate 150 includes a proximal region 401 that includes an interface area 401a configured to electrically connect the flexible membrane150 to the circuitry 421. The flexible substrate 150 is mechanically coupled to the enclosure 425 at the proximal region. A distal region 403 of the flexible membrane 150 comprises the probes 140 and a center region 402 is disposed between the proximal region 401 and the distal region 402. As illustrated in FIGS. 3B and 4, the electronics enclosure 425 is configured to be fastened to the skull, e.g., by drilling and inserting screws, while the flexible electronics sheet 150 sits on top of the cortical layers with the probes 140 penetrating the visual cortex.

In accordance with embodiments described herein, the flexible substrate 150, the array of probes 140 and the thin film circuitry 143 for addressing the probes 140 can be considered a "microsystem-on-plastic." The transducers (micro-coils and sensor tetrodes) and thin film transistor (TFTs) addressing circuits are patterned on the flexible substrate 150. After the components (sensors, micro-coils, and addressing electronics) are deposited on the substrate 150, sections of the substrate 150 are rolled up to form the probes 140. The probes 140 are located at the end of the flexible substrate 150 and are configured to penetrate into the visual cortex (V1). The probes 140 are formed by rolling up sections of the flexible substrate that support the transducers.

Figure 5:
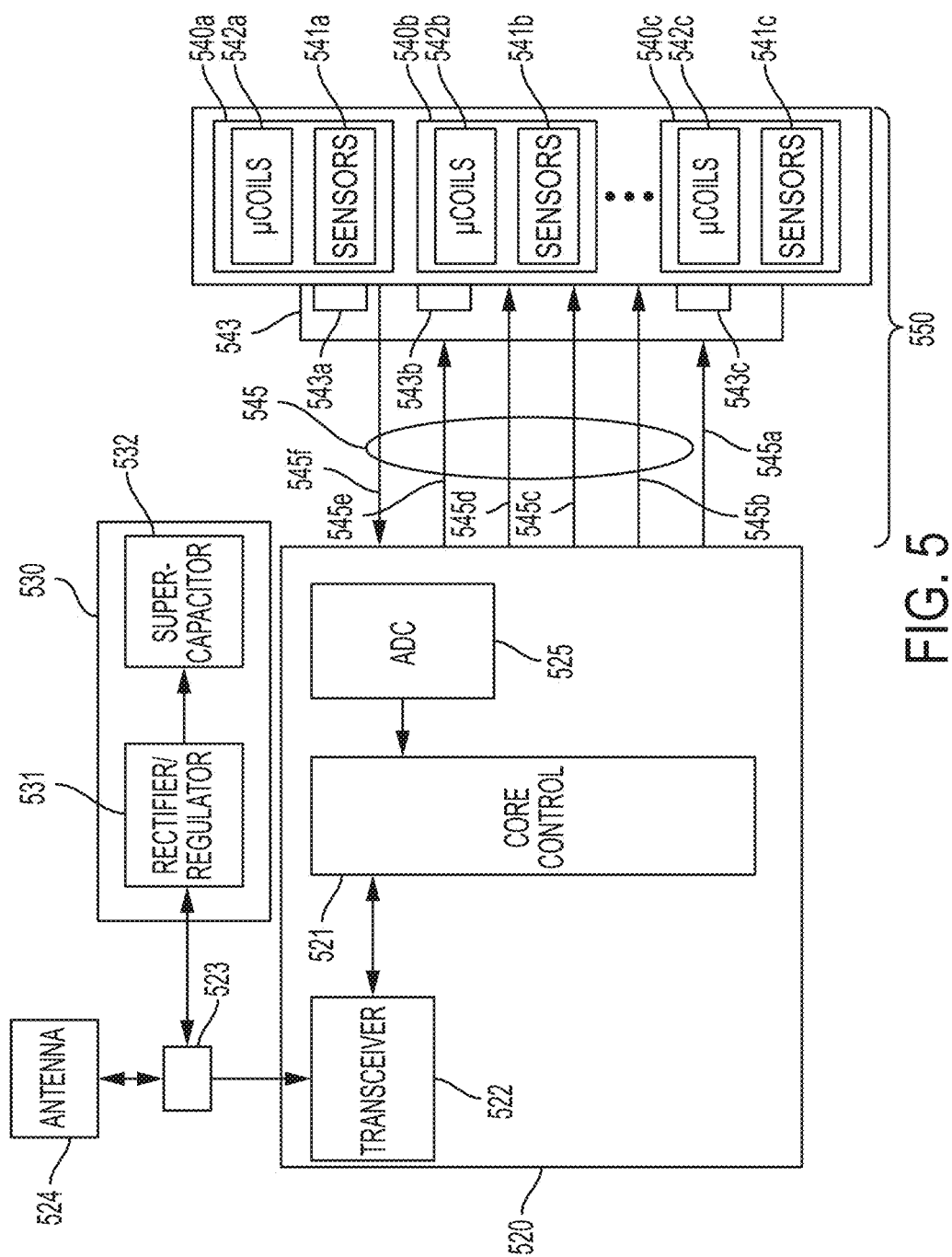
FIG. 5 is a block diagram that shows the circuitry of the internal portion of the visual prosthetic system of FIG. 1C in more detail.

FIG. 5 is a block diagram that shows the circuitry of the internal portion 102 of the visual prosthetic system 100 in more detail. As depicted in FIG. 5, the internal portion 102 of the visual prosthetic system 100 includes a plurality of neural probes 540, front end addressing electronics 543, and a neural interface bus 545, all of which are disposed on a flexible membrane. According to some implementations, the neural probes 540 include 103,680 encapsulated stimulus micro-coils 542a, b, c and 51,840 neural sensors (e.g., tetrodes) 541a, b, c organized into an 18 by 18 array of 324 probes 540a, b, c. In some arrangements, each probe 540a, b, c comprises 320 micro-coils 542a, b, c and 160 interleaved sensors 541a, b, c that connect to a neural interface bus 545 through the front end electronics 543. According to some implementations, the front end addressing electronics 543 comprises a digital gate array 543a, b, c corresponding to each probe 540a, b, c. The digital gate array 543a, b, c for the corresponding probe 540a, b, c can connect either the 320 micro-coils 542a, b, c or the 160 sensor electrodes 541a, b, c or both to the control circuitry 520.

The neural interface bus 545 may be configured to provide true bi-directional capability for any one or more of the probes 540a, b, c in the probe array 540. The neural interface bus 545 connecting the probes 540a, b, c to the control electronics 520 comprises activation lines that include a 320-line neural stimulus bus 545a, with a 10 bit stimulus address bus 545b and a 6 line stimulus control bus 545c. The stimulus address bus 545b and stimulus control bus 545c, driven by the core control module (CCM) 521 of the control circuitry 520 carry signals that select the set of one or more stimulation micro-coils 542a, b, c, that are activated. The neural stimulus bus 545a carries the signal that drives the selected micro-coils 542a, b, c.

The neural interface bus 545 also includes a 160 line neural acquisition bus 545f, with a 10 bit acquisition address bus 545d and a 6 line acquisition control bus 545e. The acquisition address bus 545d and acquisition control bus 545e are driven by the core control module (CCM) 521 to select the set of one or more neural sensors 541a, b, c, that are activated and the neural acquisition bus 545f carries the sensor signal output by the sensor 541a, b, c. The neural acquisition bus 545f is coupled to the analog to digital converter (ADC) 525 of the control circuitry 520.

The control circuitry 520 controls the selection of the micro-coils 542a, b, c and/or neural sensors 541a, b, c, as well as the waveforms of the stimulation signals used to activate the micro-coils 542a, b, c and/or the signal conditioning of the sensor signals 541a, b, c. The neural stimulus bus 545 may be configured to operate in a time division multiple access (TDMA) mode of operation with 200 µs time slots in which each probe's digital gate addressing array 543a, b, c connects the probe 540a, b, c to the neural stimulation bus 545. This enables the core control module 521 to generate a 100 µA pulse with a pulse width of 167 µs and deliver it to any one or more of the 320 coils 542a, b, c of a probe 540a, b, c. Both the current and the duration of the pulse may be modified to increase selectivity or reduce latency for the associated neuron. This configuration can stimulate the entire 103,680 coils 542a, b, c in 64.8 ms, yielding a 15.4 frames per second refresh rate or approximately 1.6 million neural stimulations per second.

The neural acquisition bus 545f will normally operate in a time division multiple access (TDMA) mode of operation with 4 ms time slots that can capture the sensor signals 541a, b, c generated by the individually stimulated neurons. These sensor signals 541a, b, c are then shunted onto the bus 545f through the probe's digital gate addressing array 543a, b, c where they are conditioned and converted to digital format in the ADCs 525 located in the control circuitry 520. This configuration enables the entire array of sensors 541a, b, c to scan all 103,680 neurons within 1.3 seconds.

The CCM 521 directs the selection of probes 540a, b, c to ensure the proper operation and response of the stimulated neurons. The probe array 540 and front end electronics 543 can complete full bi-directional transactions with 1280 neurons in 12 ms. The CCM 521 may comprise a Xilinx Spartan 6 low-power (XC6SLX35L) FPGA fabricated with a 65 nm process and contains configurable logic blocks that will operate at 1 V and 5 MHz, thereby achieving ultra-low power and thermal signature. The processing capability is more than adequate to simultaneously operate the neural interface bus 545, and ADCs 525, as well as operate the communication link with the transceiver 522 and antenna 524.

The probe array 540 may comprise about 100 to about 500 probes, e.g., about 324 probes (18×18 array), or other number of probes sufficient to stimulate about a 20 cm² region. The probes in the array 540 may be spaced apart by about 700 to about 800 µm, e.g., 750 µm to reduce damage to the brain. In some implementations, there may be about 160 electrodes and/or 320 coils per probe with 324 probes per probe array 540.

In some embodiments, the transceiver 522, which may comprise, for example, a Qualcomm WCN3680B transceiver, is capable of up to 433 Mbps data upload speeds from the CCM 521 to the patient-external device with sub-ms latencies. The transceiver 522 can receive up to 5 to 6 GHz transmissions of RF energy and signal with 256-QAM encoding from the patient-external device. The signal transmitted from the patient-external device is received through an radio frequency (RF) electromagnetic coupling, which comprises one or more micro-strip antennas 524 that are designed to transmit and receive through the skull and surrounding tissue. The electromagnetic signal received by the antenna 524 is fed into a directional coupler 523, which splits off a first portion of the received signal (power portion) to a rectifier 531 and boost converter circuit that in turn charges a supercapacitor 532. The energy in the supercapacitor 532 can be converted and regulated to enable the operation of the CCM 521, transceiver 522, front end circuitry 543, and neural probes 540. A second portion of the received signal (communication portion) carries a communication signal and is directed to the transceiver 522 for communication.

Regarding the signal power budget of the signal that links the patient-external and patient-internal devices, the RF signal from the patient-external transceiver is transmitted at a power level 27 dBm, and would be attenuated by about 4 dB through the resonant RF coupling between the patient-external and patient-internal devices. Thus, the resulting 23 dBm signal would be split in the directional coupler 523 into a near 23 dBm power signal, which would enter the rectifier 531. The communication signal enters the transceiver 522, where the receive sensitivity is −72 dBm, resulting in a 35 dB communication link margin. The uplink would be transmitted at −20 dBm, and be attenuated by about 12 dB through the RF switch and resonant coupling between the patient-internal and patient-external devices. The communication signal would then enter the external device receiver at −32 dBm yielding a 40 dB communication link margin. The data transmission bandwidth is 433 Mbps, which is achieved by using an appropriate transceiver 522, such as the WCN3680B 802.11ac from Qualcomm. In this architecture, the wide parallel neural stimulation bus 545a and the distributed gate arrays 543a, b, c would allow the 320 neurons associated with each probe 540a, b, c to be stimulated by the 320 micro-coils 542a, b, c, and subsequently read by the 160 sensor electrodes 541a, b, c. Thus, all 324 probes 540a, b, c, would be able to stimulate and read the associated neurons in the time required to cycle the neuron bus to each probe. This would result in the bidirectional read-write of all 100,000+ neurons addressed by the neural interface bus 545. For channel isolation, interlacing the stimulus and receiving transmission lines of the neural stimulus bus 545a and neural acquisition bus 545f, respectively, over a ground plane achieves about 80 dB of isolation between adjacent read channels from 300 Hz to 3 kHz, which in simulations has been determined to be the normal operating range of the neural acquisition bus 545f. Thus, according to this particular example, the power budget for the system can be less than about 120 mW.

The CCM 521 and the power management module 530 may be packaged together in a traditional hermetic package. Given the need to transmit RF data through the package, at least one face of the package may be ceramic. The package will also include metallic features to allow for hermetic welding. The transducer module package, which includes the flexible membrane 550, front end circuitry 543, and probes 540 can be hermetic or semi-hermetic. In some embodiments, the transducer module is expected to be coated with a combination of parylene and silicon dioxide. Given the performance requirements of the transducer module, this packaging strategy is expected to provide sufficient protection from body fluids.

In lieu of the use of traditional hermetic packaging (e.g., ceramic and metallic), an alternate packaging option for modules of the patient-internal device may be polymer encapsulation. In particular, combining polymer encapsulants with different properties (i.e., epoxy, silicone, or parylene) can provide significant protection against electrical shorts, material leaching, and corrosion. All mechanical packages are designed to pass hermetic leak testing, e.g. per MIL-STD-883, or via visual inspection and soak testing.

Figure 6A:
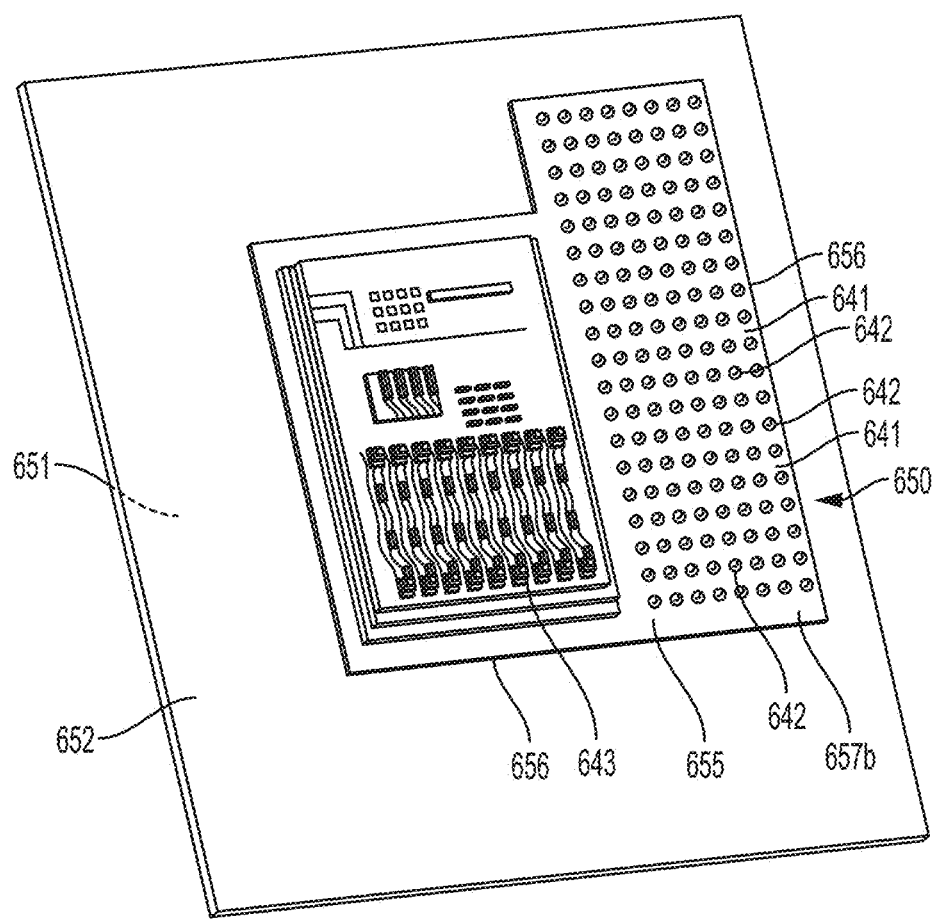
FIGS. 6A through 6D illustrate fabrication of a neural probe in accordance with some embodiments.

FIGS. 6A through 6D illustrate fabrication of a neural probe in accordance with some embodiments. The neural probe fabrication process includes deposition of electronic components, including neural sensors, neural stimulators, and front end electronics in a probe area 655 of the flexible substrate 650, e.g., a polyimide membrane. As indicated in FIG. 6A, in some embodiments, the neural sensors 641 and stimulators 642 are formed on a first surface 651 of the flexible substrate 650 and the front end electronics 643 are formed on an opposing, second surface 652 of the probe area 655 of the flexible substrate 650. When laid flat, the probe area has a surface area of about 0.0048 $cm^2$ to about 0.032 $cm^2$. The probe area may contain about 250 to about 450 neural stimulators and/or about 250 to about 450 neural sensors. In some embodiments, the neural sensors 641 are disposed on the first surface 651 of the flexible membrane 650 and the micro coils and electronics are disposed on the second surface 652 of the flexible membrane 650. As previously discussed, the neural sensors 641 may comprise tetrodes and the neural stimulators 642 may comprise three dimensional micro-coils. In some embodiments, the front end electronics 643 may include TFTS used as switches for selecting the neural sensors 641 and stimulators 642. In some embodiments, the front end electronics 643 may comprise TFT-based shift registers, logical circuits, and/or multiplexers, etc.

Figure 6B:
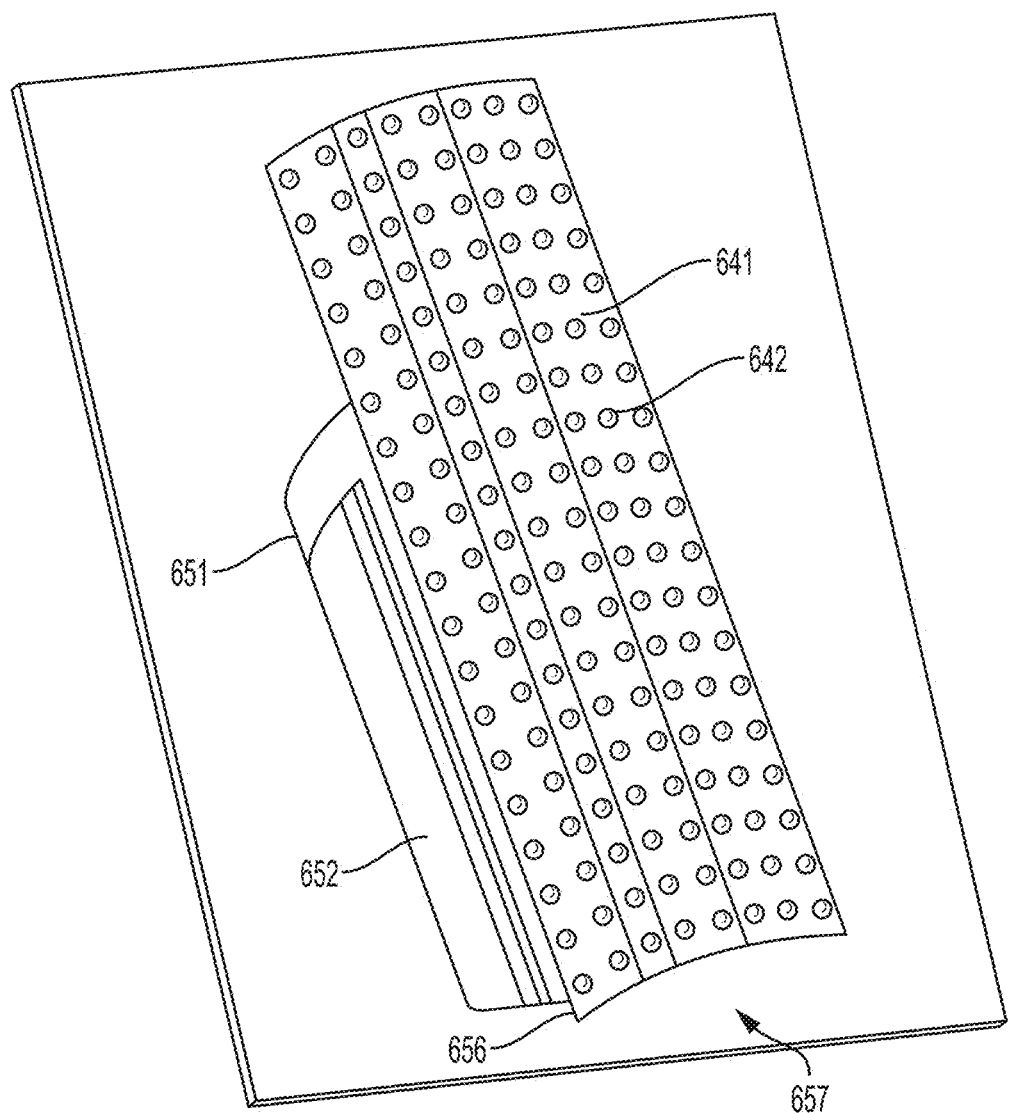

Before or after deposition of the sensors 641, stimulation coils 642, and electronics 643, the probe area 655 is detached from other areas of the flexible membrane 650 (except for a bridge). The probe area 655 may be detached by laser or die cutting along a majority of the perimeter 656 of the probe area 655. The probe area 655 of the flexible membrane 650 is separated from the rest of the flexible membrane 650 at the cut perimeter 656 and remains attached to the rest of the flexible membrane 650 by at least one uncut section of the perimeter, referred to herein as a bridge 657b. After deposition of components 641, 642, 643 in the probe area 655 of the flexible membrane 650 and cutting the perimeter 656, the flexible membrane 650 can be rolled up or folded to form a three dimensional probe 640. In some embodiments, after the probe area 655 is rolled up, the neural sensors 641 are disposed on the exterior surface of the probe 640. The neural stimulators 642 and front end electronics 643 are disposed on the interior surface of the probe 640 such that the neural stimulators 642 and front end electronics 643 are protected within the interior of the probe 640. In some embodiments, after the probe area 655 is rolled up, the neural sensors 641 and the neural stimulators 642 are disposed on the outer surface of the probe 640. The front end electronics 643 are disposed on the inner surface of the probe 640 such that the front end electronics 643 are protected within the interior of the probe 640. FIG. 6B illustrates the flexible membrane 650 as it is being rolled up into a probe 640. The exterior surface of the probe 640 comprises at least a portion of the first surface of the flexible substrate and the interior surface of the probe 640 comprises at least a portion of the second surface of the flexible substrate.

Figure 6C:
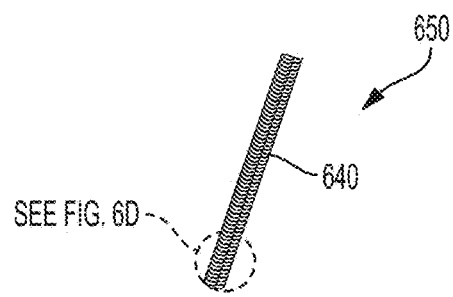
Figure 6D:
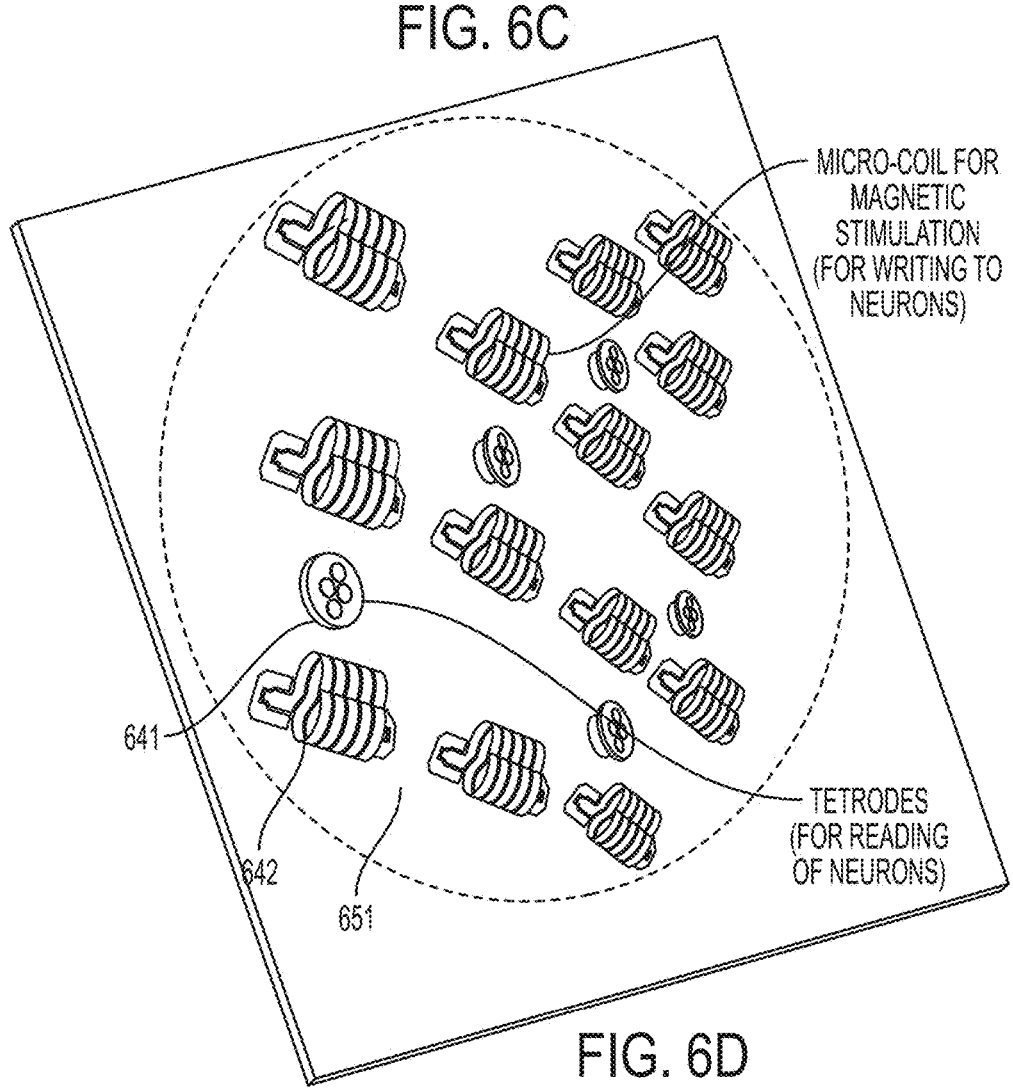

FIG. 6C shows the rolled up probe 640 attached by the bridge 657b to the rest of the flexible membrane 650. The probe 640 is oriented at an angle, e.g., about a 90 degree angle, to the plane of the rest of the flexible membrane 650 at the bridge 657b and can penetrate the dura matter of the brain while being supported by the rest of the flexible membrane 650. FIG. 6D is a close up view of the external surface 651 of the probe 640 showing neural sensors 641 intermingled with neural transmitters 642. The external surface 651 of the probes 640 is comprised of a periodic array of micro-coils 642 which are configured to stimulate the neurons of the visual cortex and tetrodes 641 which are configured to sense the neurons of the visual cortex.

The flexible membrane 650 provides a flexible electronics substrate. The flexible membrane 650 may have a thickness between about 2 μm to about 10 μm, e.g., in some embodiments, the flexible membrane 650 has a thickness of about 4 μm. Despite being so thin, the flexible membrane 650 has adequate strength to be self supporting. The rolled up probes 640 may have a diameter of between 10 μm to 100 μm, e.g., the probes may be about 30 μm in diameter in some embodiments. The probes 640 can have a length of about 1 mm to about 3 mm, or about 1.4 mm to about 2 mm, or about 1.6 mm, for example. The probes 640 have a length that allows penetration deep enough to reach intracortical layers 5 and 6.

Writing to neurons is accomplished by magnetic stimulation using the array of micro-coils 642. Reading the neurons is achieved by sensing neural signals using the electrically-isolated tetrodes 641. The neural sensors may be in contact with the visual cortex. In contrast, the neural stimulators need not be in direct contact with the visual cortex.

The tetrodes may be cylindrical patches about 2 to 10 μm in diameter, or square regions of about 2 to 5 μm by about 2 to 5 μm, and about 2 to 10 μm tall. The tetrodes can have an area of about 25 μm, for example. In some embodiments, the tetrodes 641 are about 5 μm in diameter and about 5 μm tall. The tetrode sensors 641 and electronics 643 can be formed using standard optical lithography.

The micro-coils 642 may be between about 10 μm to 30 μm or about 15 μm to about 25 μm in diameter and length. For example, in some embodiments, the micro-coils 642 may be about 20 μm in diameter and length, having an area of about 400 $μm^2$.

The 3D micro-coils 642 can be formed using stress-engineered materials as discussed in more detail below. According to some embodiments, the 3D micro-coils 642 comprise MoCr films which are sputter-deposited with a built-in stress gradient such that when patterned and released from their substrate, they curl into a designed radius of curvature. The scaffolds are then electroplated with copper to form highly conductive coil windings. Coils of radius curvature of about 10-20 μm can be fabricated by controlling parameters of beam length, width, thickness and strain gradient and suitable as stimulation transducers for the vision prosthetic system.

Figure 7A:
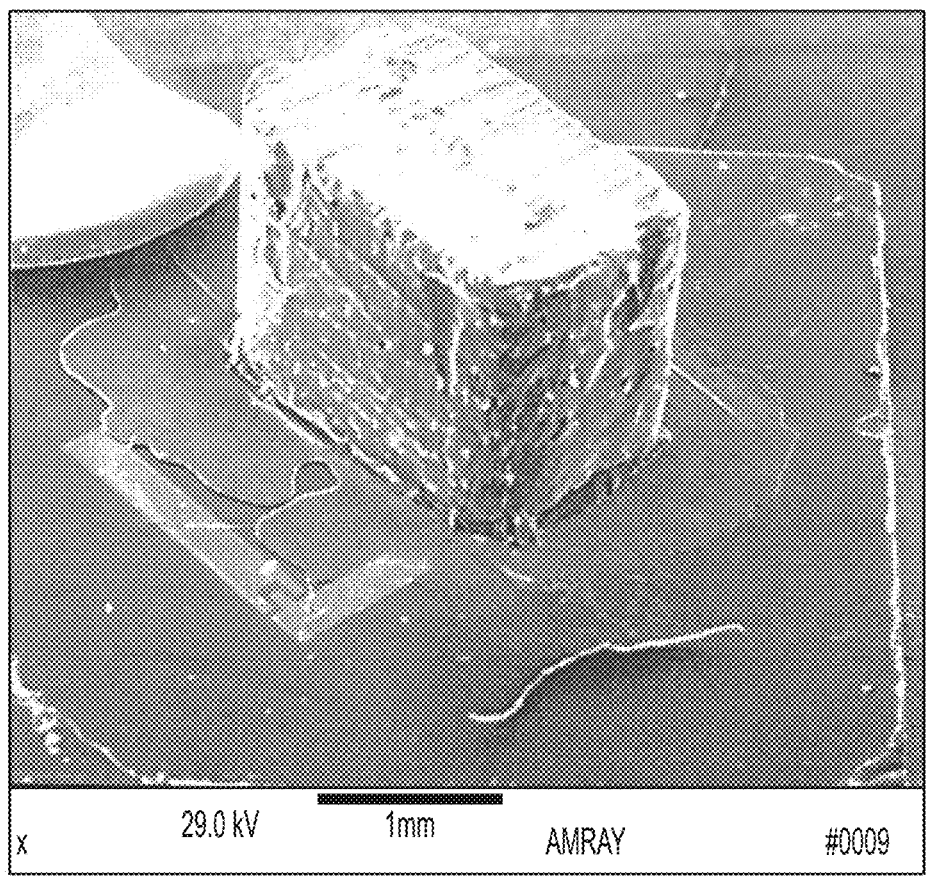
FIG. 7A is a scanning electron microscope (SEM) image of a micro-coil stimulator (less than 1 mm in diameter) encapsulated in Teflon by a patterned mold process in accordance with some embodiments.
Figure 7B:
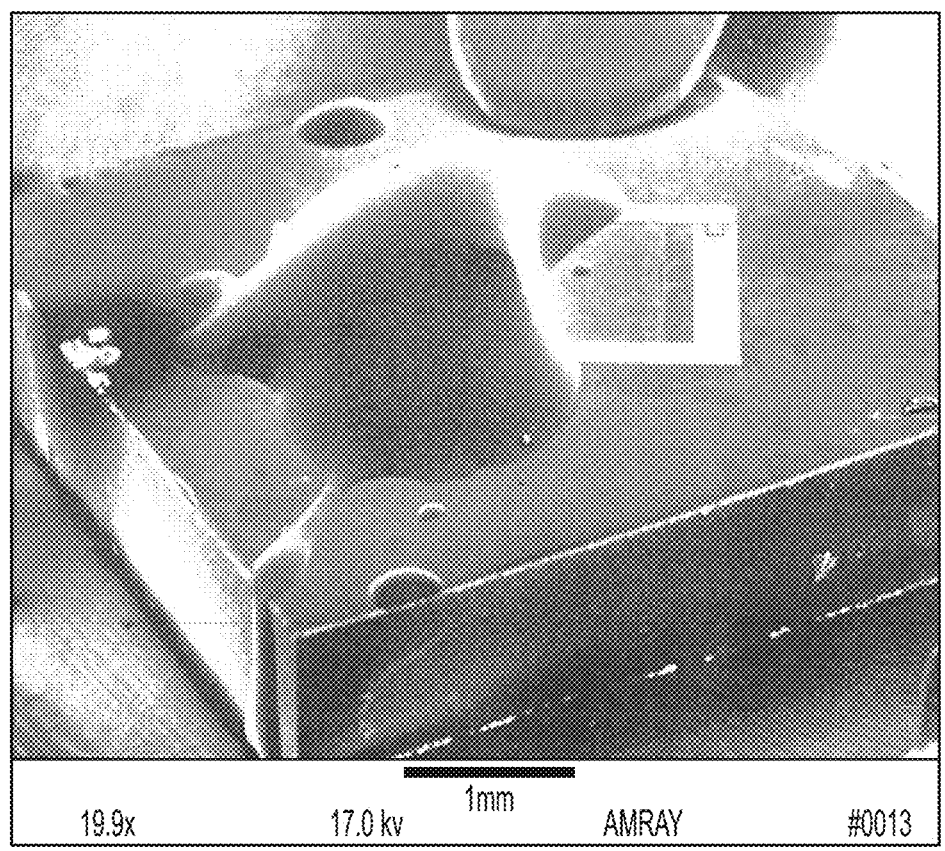
FIG. 7B is a SEM image of a micro-coil stimulator (less than 1 mm in diameter) encapsulated in the electronics packaging polymer DEXTER HYSOL 6511 in accordance with some embodiments.

There are a variety of options for coating the coils to ensure robustness. FIGS. 7A and 7B show two methods of coating which result in rugged coils, allowing the coils to survive electronic die tests, such as drops on hard surfaces from heights of over 1 m.

FIG. 7A is a scanning electron microscope (SEM) image of a micro-coil stimulator (less than 1 mm in diameter) encapsulated in Teflon by a patterned mold process. FIG. 7B is a SEM image of a micro-coil stimulator (less than 1 mm in diameter) encapsulated in the electronics packaging polymer DEXTER HYSOL 6511.

The probe 640 can be rolled up by strain engineering. The polyimide membrane supporting the sensors, stimulators, and electronics can be rolled in about 30 to about 100 μm diameter cylinders using a bottom-up process, which is conceptually similar to the process used to produce the stressed metal coils as discussed below. Compared to top-down rolling the polyimide membrane using external forces (e.g., rolling by hand), a bottom-up process improves reproducibility and scalability.

Figure 8:
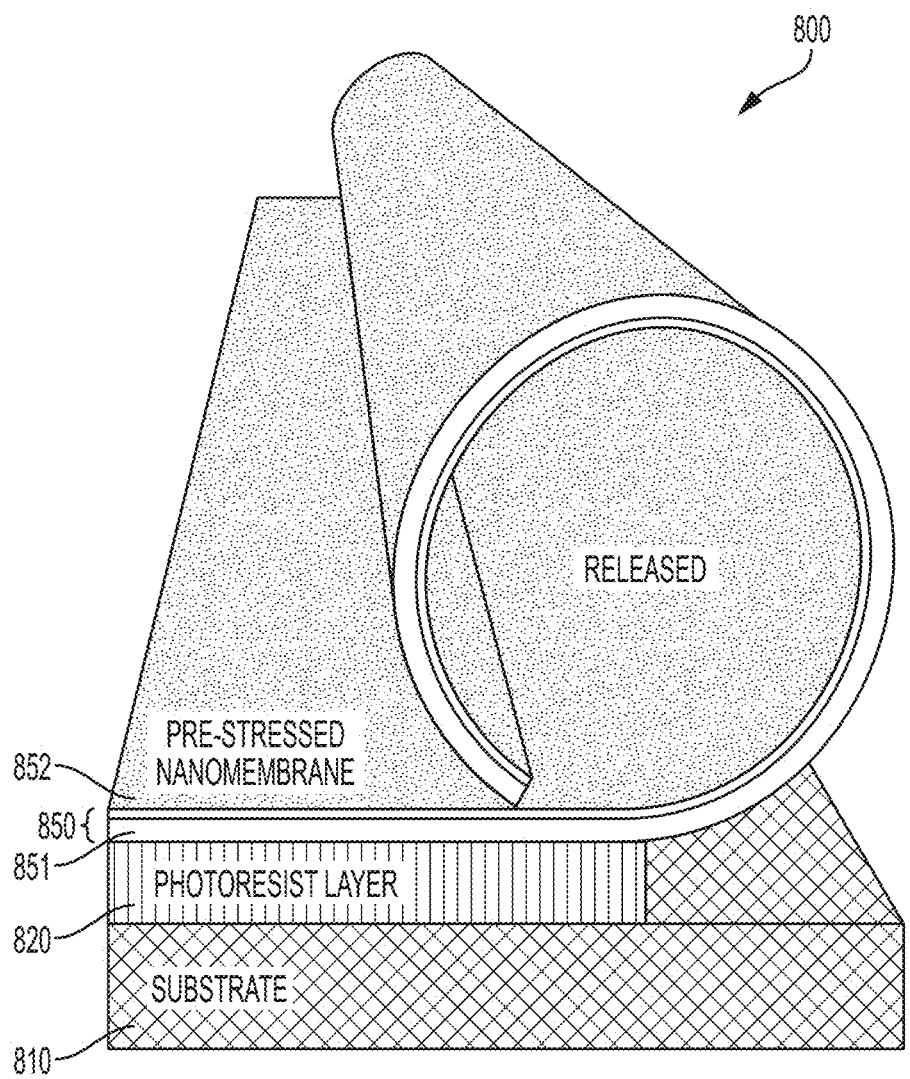
FIG. 8 illustrates a stress-engineered subassembly that allows for rolling of the flexible substrate to form a probe in accordance with some embodiments.

FIG. 8 illustrates a stress-engineered subassembly 800 that allows for rolling of the flexible membrane to form a probe. The subassembly 800 includes a substrate 810, wherein the substrate is rigid compared to the membrane 850. A release layer 820 comprising photoresist or other suitable release material, is formed on the substrate 810. The material of the flexible membrane 850 is disposed on the release layer 820. The flexible membrane 850 includes a polyimide layer 851 and a hydrogel layer 852. When the release layer 820 is removed, e.g., by etching, the hydrogel layer 852 is configured to contract by de-swelling after the polyimide 851 has been released from the rigid substrate 810. Contraction of the hydrogel layer 852 causes the flexible membrane 850 including the polyimide membrane 851 to roll. The diameter of the roll is determined by the strain state in the flexible membrane 850 and its thickness, which can be controlled by layer synthesis parameters and de-swelling conditions.

Thin film devices on rolled-up polymers have been fabricated with controlled and reproducible diameters ranging from 10 to 150 μm. Rolling of the polymer can be accomplished without substantial impact to the components supported on the membrane.

Figure 9A:
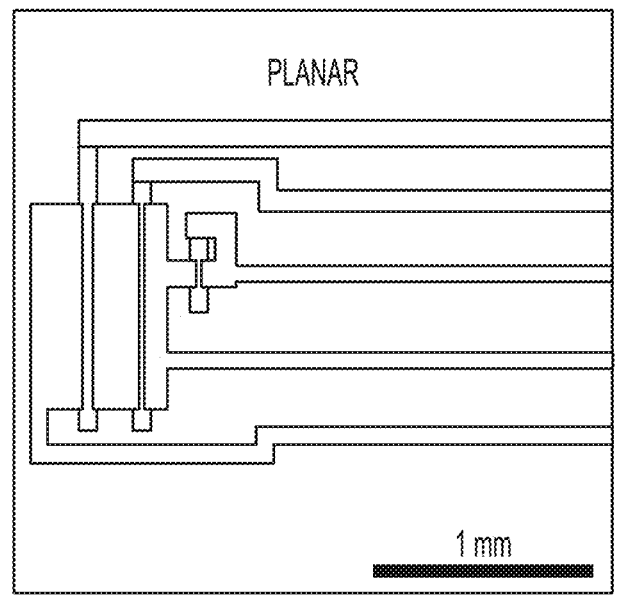
FIGS. 9A and 9B respectively show a flat flexible membrane that includes electronic circuitry and electrically conductive wiring disposed thereon and the flexible membrane after it is rolled up as a neural probe in accordance with some embodiments.
Figure 9B:
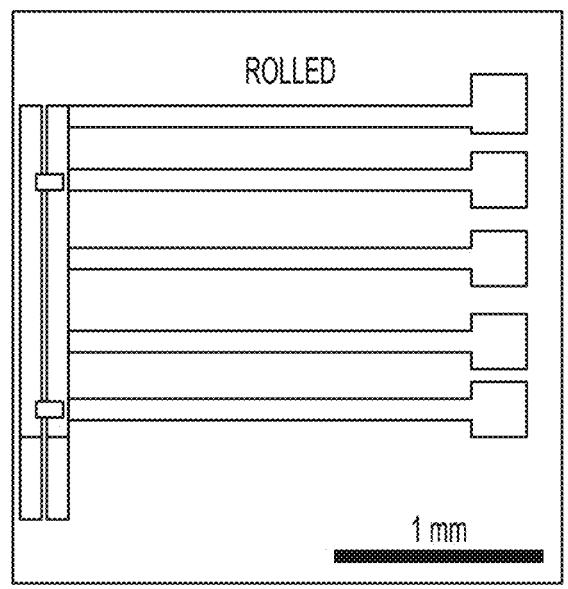
Figure 9C:
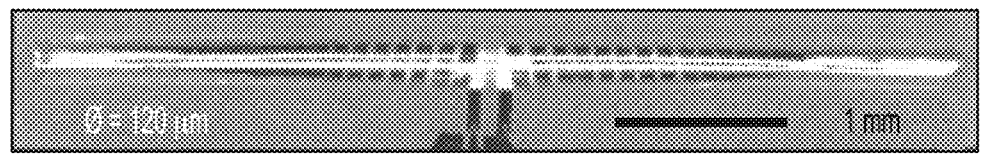
FIG. 9C shows a 120 μm diameter polyimide membrane suitable for a neural probe in accordance with some embodiments.
Figure 9D:
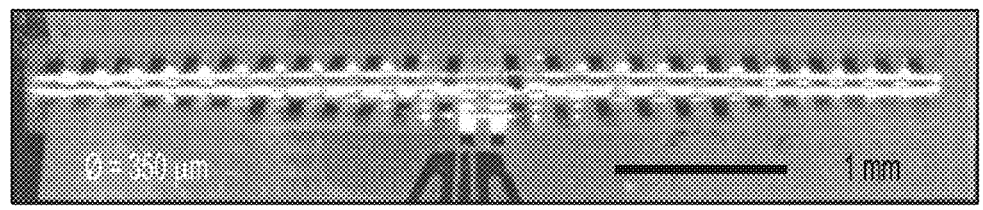
FIG. 9D shows a 350 μm diameter polyimide membrane suitable for a neural probe in accordance with some embodiments.

FIGS. 9A and 9B respectively show a flat flexible membrane that includes electronic circuitry and electrically conductive wiring disposed thereon and the flexible membrane after it is rolled up as a neural probe. FIG. 9C shows a 120 μm diameter polyimide membrane suitable for a neural probe. FIG. 9D shows a 350 μm diameter polyimide membrane suitable for a neural probe.

Figure 10:
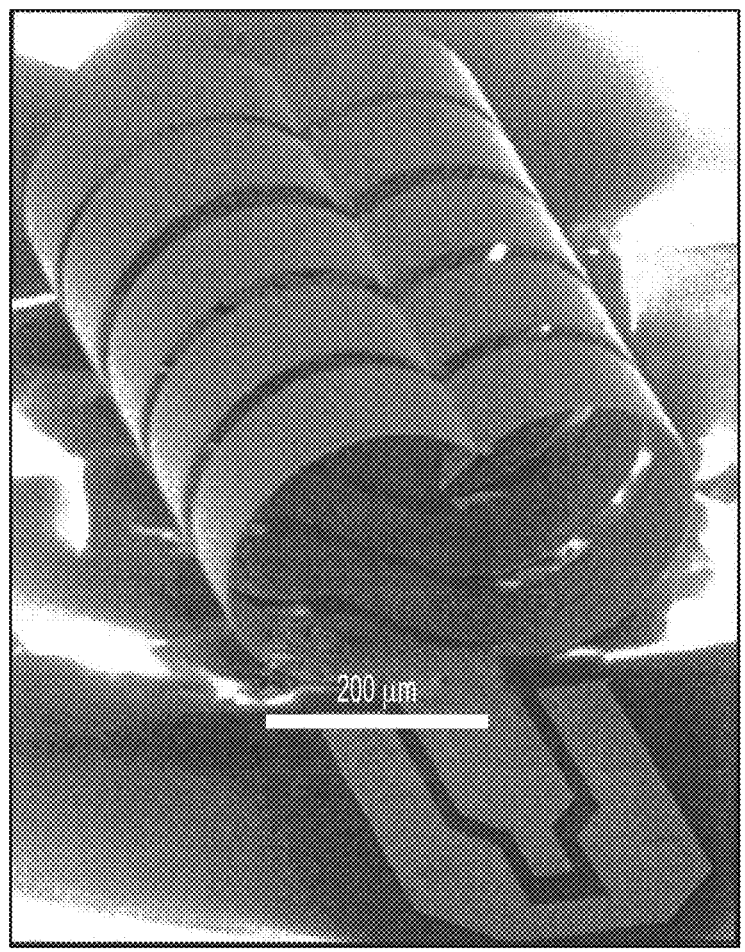
FIG. 10 is an image of a 3D coil which is suitable for use as a neural stimulator in accordance with some embodiments.

FIG. 10 is an image of a 3D coil which is suitable for use as a neural stimulator. Out-of-plane 3D coil structures place the coil axis parallel, rather than perpendicular, to the substrate plane. The 3D coils can be formed from materials that have a built-in stress profile. The stress profile can designed into a thin film by varying the growth conditions appropriately during deposition to produce coil structures which include released elastic members that bend back on themselves and contact the substrate producing loop windings of the coil. Preferably the elastic member is formed of a conductive material. Alternatively, one or more layers of conductive metal, such as gold, copper or silver, may be formed on an inner surface, an outer surface, or both surfaces of a non-conductive layer. By using or adding one or more conductive layers, a coil structure suitable for use as a neural stimulator can be manufactured. Further details regarding 3D coil structures and methods of making 3D coils structures are described in U.S. Pat. Nos. 6,392,525, 6,534,249, and 6,856,225 which are incorporated herein by reference.

An out-of-plane coil structure comprises a substrate with elastic members, each elastic member having at least one anchor portion fixed to the substrate and an elastic portion that, when released from the substrate, forms a full or half loop of the 3D coil. The elastic portion is initially attached to the substrate, but after it is released from the substrate curves to form at least a portion of a coil loop due to the stress profile in the elastic member. Out-of-plane coils as shown in FIG. 10 are formed by closing half loop pairs of elastic members. Upon release of the released portion of the elastic member, the half loop pairs need only to be coarsely aligned to each other and connected together, such as by either plating or soldering. The loop halves need not be the same length. One side could be longer than the other to facilitate the overlap. A different release material may be used under each loop half to release the loop halves sequentially.

According to some embodiments, the elastic members may form the whole loop and may include a second anchor portion that is connected to the substrate as described in more detail below. The second anchor portion and the loop winding are initially fixed to the substrate, but are released from the substrate to become separated from the substrate. An intrinsic stress profile in the elastic member biases the second anchor portion away from the substrate forming the loop winding and causing the second anchor portion to contact the substrate. The resulting coil structure is out-of-the plane of the substrate. The loop winding may also include a plurality of turns.

Various techniques may be used to position the second anchor portion away from the takeoff point of the elastic member, either tangentially or axially. If the second anchor point is positioned tangentially from the takeoff point, the loop winding is generally in the shape of a distorted circle, i.e., the second anchor portion contacts the substrate in the same vertical plane as the first anchor portion. Various techniques may be used to position the second anchor portion tangentially from the takeoff point. For example, a mechanical stop can be fixed to the substrate at the desired location to catch the second anchor point while it is detached from the substrate. Also, the radius of curvature of the elastic member may be varied, such as by adding a load layer onto a portion of the elastic member or by patterning one or more openings or perforations into a portion of the elastic member. Various techniques can be used to connect the second anchor portion to the substrate. For example, the second anchor portion can be soldered or plated to the substrate. Each anchor portion can be attached to a metal contact pad attached to the substrate, for providing electrical connectivity to other elements in a circuit.

One difficulty in creating out-of-plane structures is ensuring that the elastic members used to form the loops are not bunched or entangled by hydrodynamic and surface tension forces when they are being released. It has been observed that aqueous release and drying of the released elastic members causes insufficiently stiff fingers to get pulled around by the air liquid interface and stick together. The longer and narrower the released elastic members the greater is the problem. A related defect occurs when released elastic members intertwine. Another difficulty is providing enough contact area for the free end of the released elastic member where it makes mechanical contact for subsequent electroforming. A further difficulty is calibrating and maintaining the stress parameters in the metal deposition process in order to keep the diameter of the coil, and as such its inductance, within a few percent tolerance.

Figure 11:
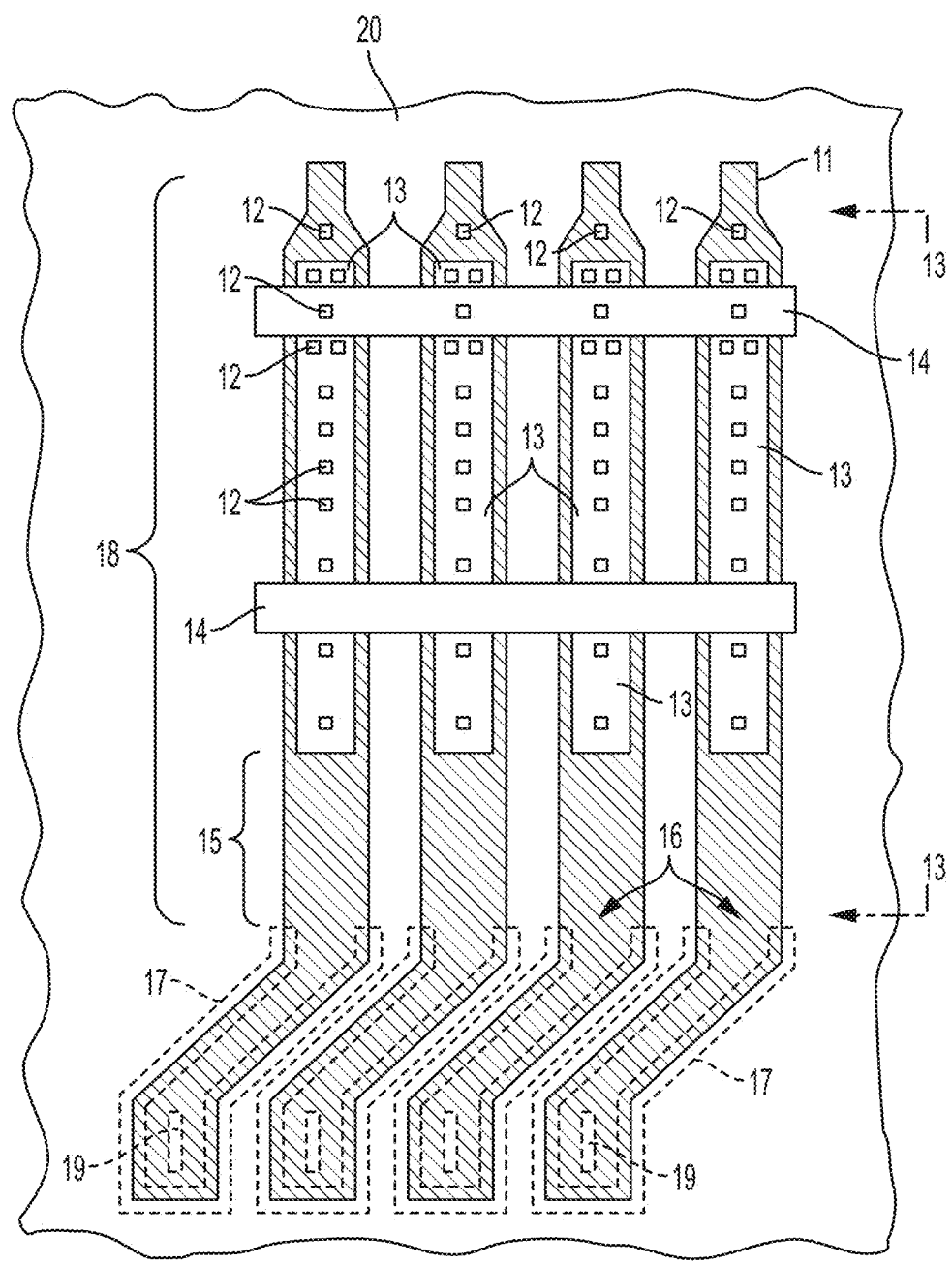
FIG. 11 is a top view of a layout of four tethered elastic members before release in accordance with some embodiments.
Figure 12:
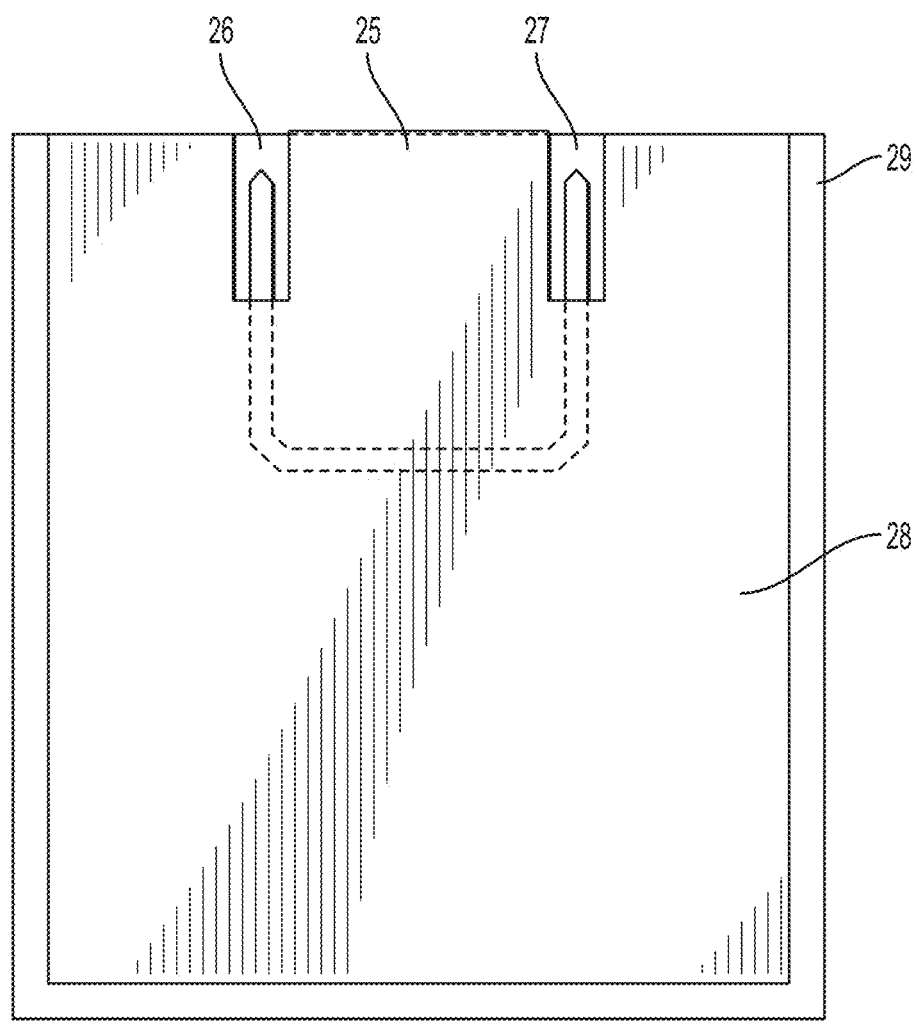
FIG. 12 is a top view detail of a raised mechanical stop on a contact pad in accordance with some embodiments.
Figure 13:
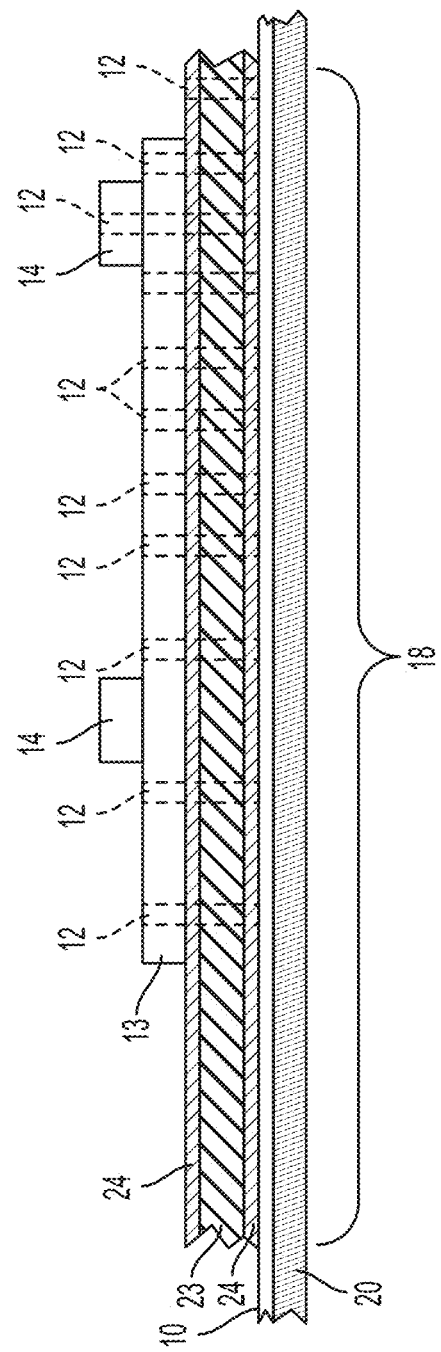
FIG. 13 is a cross section along line 3-3 of the layout of FIG. 11.

FIGS. 11 through 15 illustrate methods of making the 3D coil structures for neural stimulation. Referring to FIGS. 11 and 13, a release layer 10 such as Ti, Si, or SiN is patterned on membrane 20. The membrane may be any material that is flexible and suitable for rolling or folding into a neural probe. The release layer 10 may be a material that can be quickly removed by selective dry or wet undercut etching.

Possible etchants for a Si release layer include KOH (wet processing) and XeF$_2$ (dry processing). Hydrofluoric acid will etch Ti or SiN release layers.

A layer of an elastic material is deposited on substrate 20 and patterned into four individual elastic members or fingers 18. Each finger 18 can be formed of a single elastic material 23, such as a stress graded film of NiZr, Mo/Cr, solder-wettable Ni, or other suitable material. Alternatively, each finger 18 can be formed of two or three layers: a bottom gold layer 24, for example, can be used to form the outer skin of the coil when released and provides a high conductivity path for electrons at high frequencies. A second gold layer (not shown) can be deposited on top of layer 23 to passivate the surface. The added layers may also serve as a seed layer for subsequent plating. Depending on the design required, any metals capable of holding large stresses may be used to form the parts of the finger that induce bending, and clad them with additional layers that are good seed layers for plating. Alternately, the stresses may be placed into a material that contains the required bending moment and is also suitable for plating or soldering, for example Ni or its solution hardened alloys.

Figure 16:
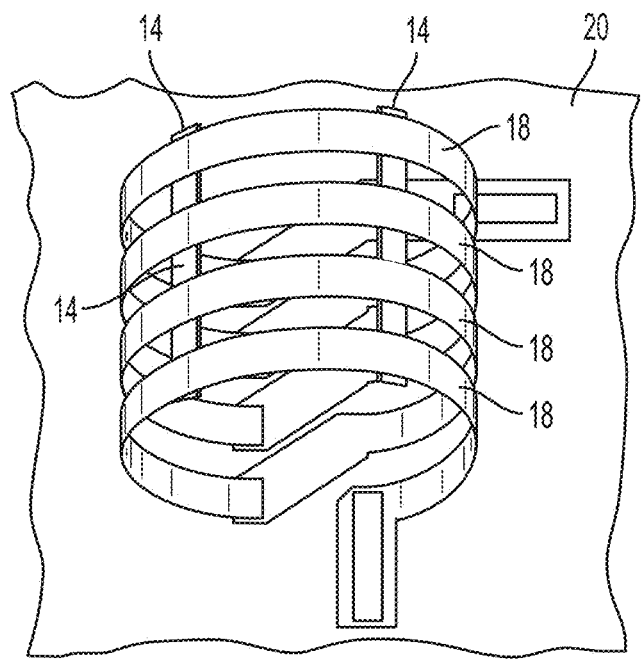
FIG. 16 is a partial perspective view of the tethered elastic members of FIG. 11 after release and formation of coil structures.

Referring to FIG. 11, two cross tethers 14 were deposited and patterned to connect or join at least from one released elastic member 18 in the array of four fingers 18 to one additional released elastic member 18 in the array. Tethers 14 are shown as substantially perpendicular to the length of members 18, but may be disposed diagonally or some other convenient orientation for maintaining the spaced-apart separation of the released elastic members. The release mask 17 allows a release etch to undercut both the released elastic members 18 and the tether 14. Although two tethers 14 are shown in FIGS. 11 and 13, only one may be used or more than two may be used. The tether 14 may be perforated with one or more perforations 12 to allow release etchant to pass through the tether layer 14 through an aligned hole 12 in the elastic member layer 18 in order to more rapidly release the finger 18. In FIG. 11, a tether layer 14 is placed near the four tips 11; a second tether layer 14 is placed near the center of the fingers 18. FIG. 16 shows the released coils formed into connected coils 18 with tether layers 14 still in place.

The tether layers minimize or eliminate the floppiness problem of very long flexible released elastic members (the longer the released elastic members, generally the greater the problem). Longer, thinner released elastic members also have a tendency to intertwine after release. By placing cross-tethers on the elastic members that release along with the elastic members, this problem is also eliminated. The tethers are made narrow enough to ensure that release etch releases them along with the elastic members. The tethers maintain uniform released elastic member element array spacing and prevent the released elastic members from touching or entangling after release and when the tips are being connected to their respective pads. The ensemble of tethered released elastic members behaves like an effectively stiffer structure. The tether material should be non-conducting in order to provide electrical isolation of electrically conductive released elastic members.

The out-of-plane coil structures are particularly beneficial when used as inductors or transformers in integrated circuits. While the individual released elastic members may be formed of a metal stress graded material, or multi-layers of metal and stress graded material, in many applications, the structure will be plated with metal in a plating bath after the released elastic members are released and the free ends connected to the contact pads. As described below, resist reflow is used to protect certain areas of the structure from the plating bath. The reflow step could also be used to reflow the tethering material, particularly if the tether material is the same as the reflow material. If the amount of reflow is too large, the tethers could neck down and even separate into drops of resist on each finger. To avoid this, a separate mask can be used to define the tether layer, or the tether layer can be combined with the load layer (if a load layer is added to the structure—as described below) into a single layer separate from the release layer. If, for example, the release layer is made of resist, the tether-load layer could be made of polyimide. Reflow of the resist would not reflow the polyimide, because of the wide separation of their glass transition temperatures.

When a separate tether-load layer material is used, when the release window 16 is removed the exposed release metal that was used as a common cathode can be cleared away. The tethers may remain in place for this and subsequent dicing and packaging steps because although the plating step stiffens the released elastic members, once the tethers are removed, individual released elastic member loops may bend into adjacent loops. The tethers can and will typically be removed after electroforming. However, there may be some applications where it will be appropriate to leave the tethers in place.

If the tethers are combined into the release window mask, no added mask count is needed to implement the tether layer, making it effectively zero cost. The tethers proposed can be implemented in the release window material that in the process flow serves to define where the released elastic members lift and also where the electroplating occurs. If the tethers are not combined with the release mask, then a three mask process may be needed, which is still possible to implement at low cost.

The rate of Ti release layer undercut below both released elastic member metal and photoresist has been characterized. The undercut rate in the release etch under both released elastic member and tether materials is identical and rapid. Release times for released elastic members with 200 nm Ti is on the order of 0.34 microns/sec, meaning that 50 micron wide released elastic members take about 74 seconds to release. Tethers narrower than 50 microns will release during the same process. Much narrower tethers may be used, on the order of 20 microns; these tethers will interfere even less with the release process. Tethering effectively reduces the length-over-width ratio of the released elastic member segment. The inventors have demonstrated that 100% yield without bunching or tangling is routine if length/width limits are not exceeded.

After release and coil closure, the tethers are located on the inside of the coil. At high frequencies, currents flow on the outside of the coil (made of an electrically conductive material) due to the skin effect. To avoid shorting between adjacent coils formed of an electrically conductive material, the tether material should be made of a non-conductive material. No plating will occur where an insulating tether resides, however this will have no significant electrical effect on the final device.

In accordance with another embodiment, a graded density of perforations 12 disposed along the length of the spring 18 may be used to control the rate of release of the released elastic members 18. FIGS. 11 and 13 show one way in which a graded perforation density may appear in the layout of a coiled spring array. Note that the spacing between perforations 12 is increased gradually from the tip 11 to the base of the released elastic member 18. Note also that, if a load layer 13 (described below) is also present, perforations 12 in the loaded section 13 of the beam 18 go through both the load layer and elastic member layers 23 and 24.

The graded perforation density in elastic members 18 enables the release from the substrate to be in a controlled fashion starting with the tip 11, and progressing toward the base. This is important because of the large amount of elastic energy that is stored in the elastic member before release. If the release rate of the energy is too rapid, the elastic member can reach enough speed to entangle with other elastic members or break. Gradual release of the elastic member allows mechanical damping enough time to limit the total kinetic energy of the spring to a non-destructive level.

Perforations may also be used to create varied inductance values from one individual coil to another or from a series of coils to another. Typically, for a given thin film deposition sequence, only one coil area is created. This happens because typically only one main radius is created, and if a load layer is used, one loaded radius. To obtain different inductance values, the number and pitch of the windings must be varied. The number of windings can only be varied discretely, hence, the pitch must be used to fine tune inductance values for a given loop area. If a design calls for more than one inductance, then there will be varied finger widths. To ensure that the fingers all release at approximately the same time, with the same release layer undercut, the use of graded density perforations, with the same approximate densities is required. The graded perforation density can be used to ensure that all elastic members release at the same rate, regardless of width.

Tethers may be used in addition to the graded perforation density. In some cases, it may be possible to locate the tether layers in between perforations. In other cases however, if the tether must pass over a perforation, that area of the tether must be either removed or perforated so that the release etch is not blocked. If a load layer is present, the perforation should pass through the load layer so that release etch is not blocked. Any structure pertaining to the load layer that is present during elastic member release must not block the release etch from passing through the elastic member perforations. This typically calls for making perforations in both the spring definition mask and in the load layer definition mask in order to define an operational perforation 12.

Load layers have been used to vary the radius of curvature of the elastic member. The load layer 13 is an additional layer patterned on the elastic member 18 to apply stress that either increases or decreases the bending radius. The load layer 13 is patterned to reside generally in the middle segment of the elastic member 18. The load layer is typically made of metal, such as gold, Mo, MoCr alloy, Ni, Ni alloy etc.

A load layer 13 made of a reflow material such as photoresist can be advantageously used to load elastic members 18 to increase the radius in comparison to the same beam without the resist. The resist can be introduced in the same masking step that creates the release window, or it can be introduced in a separate step. The resist has very low intrinsic stress when it is processed. Once the spring is released, the resist is typically on the inside of the bending cantilever, and therefore it accumulates compressive stress as it opposes the bending. One desirable feature of the resist is that the loading effect of the resist can be gradually changed with either heat or plasma ashing. Heat permits the resist to soften, and above its glass transition temperature, to flow. For Shipley 1813 resist, it was observed that the loading effect was substantially reduced at 185 C, and was further reduced at 200 C. The loading effect can be substantial. In one experiment, the inventors altered the released elastic member diameter from 495 down to 345 microns.

Plasma ashing of the photoresist load layer 13 is another way to control the released elastic member diameter. Ashing permits gradual controlled reduction of the resist thickness without attacking the spring metal. As the resist thickness is reduced, the diameter shrinks.

The resist defining the release window will typically be reflowed in order to seal off the edge of the release metal to block plating along the edge of the window. This reflow step may relax some or all of the load created by the loading resist. If desired, the load layer resist and the release window resist can be two separate materials with different glass transition temperatures.

Using a load layer formed of a reflow material such as resist, increases the stiffness and radius of the released elastic members while they are still in the release etch. Once the released elastic members are removed and dried, the reflow step tightens the radii. This can be performed in air, where there is reduced likelihood of sticking or entangling. The trajectory of the free end of each cantilever is therefore determined by a two step process of first releasing the elastic member and then reflowing a reflow load on the released elastic member. This two step trajectory is preferred because the step of placing the tip to its target contact point can be done slowly and in air in the absence of surface tension forces.

A load layer of sputtered material, preferably metal can be introduced to produce a loaded section of an acircular beam. The loading effect of the metal can be controlled by selecting the layer thickness, intrinsic stress and modulus. Since it is desirable to keep the layers thin in order to minimize etch times and undercut, utilization of non-zero stress to minimize the amount of metal needed may be advantageous. For a given material, the elastic modulus is fixed, however, the stress may be controlled to minimize the required thickness. For example, a compressive load applied to the inside surface of a beading beam will expand the radius of the beam more than a neutral or tensile load.

The width of the load layer can be varied in order to adjust the amount of change induced in the released elastic member. For example, by applying a load layer that exactly balances the bending moment of the released elastic member when its width equals that of the released elastic member, the radius of the loaded elastic member can be varied from infinity down to the released elastic member's natural radius by varying the width of the load layer. Different springs, or different segments within released elastic members can have different radii without introducing more than one load layer by simply altering the load layer width.

To control the thickness of the load layer and the resulting stress, the load layer may be a multilayer. The layers that comprise the released cantilever can include a bottom layer of seed metal for plating, the layers of stressed spring metal, a top layer of seed metal, a layer of load metal, and additional seed metal in case plating is desired on the loaded segment. The load layer may be fabricated from the same material as the spring metal. This simplifies the processing. All of the layers can be deposited in the same deposition apparatus by sequential deposition.

Gold can be used as the seed metal for plating. The seed metal will have some loading effect of its own. It is possible therefore to load the beam with the multiple layers of seed metal. Gold is soft however, and has a smaller modulus and yield stress than the metals typically used for the springs. More efficient loading can be achieved with spring metals such as MoCr. Ni and Cu are also possible seed metals for plating, and may have a cost advantage over gold.

Figure 22:
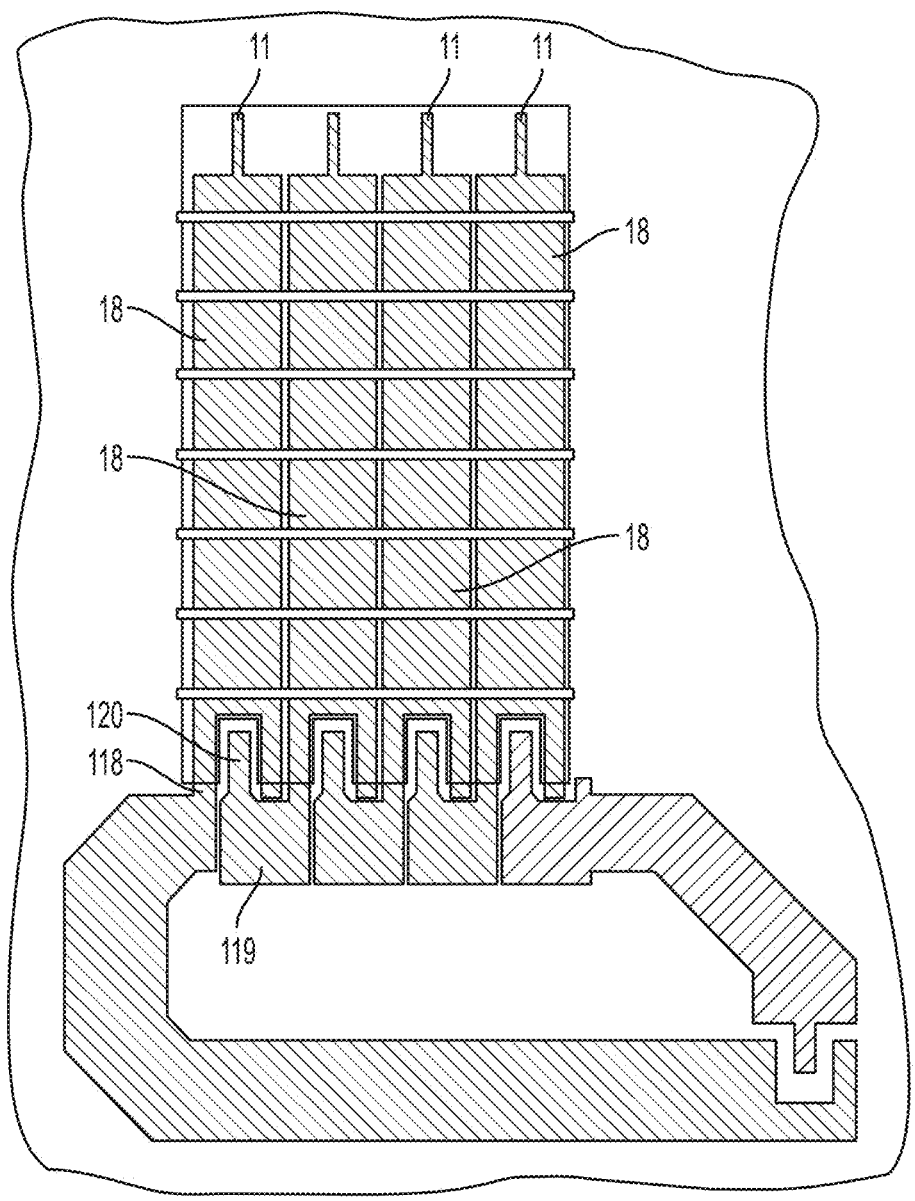
FIG. 22 is a top view of yet another alternate layout of four elastic members before release in accordance with some embodiments.

One configuration for making a multi-turn coil out of a series of individual coils is to pattern the base of the elastic member in the shape of an inverted "Y" or "U". Referring to FIG. 22, elastic members 18 include inverted base pads 118 (in the shape of a "U"). The contact pad 119 for an adjacent coil can then be positioned within the space provided by the "Y" or "U" configuration of base pad 118. One way to increase the yield of the Y-spot loop (as described in the '815 application) is to extend a narrow tip 11 on the elastic member 18 to allow this tip 11 to bisect an extended portion 120 of the Y past the contact pad 119. This permits coil completion without shorting, even if the radius is tighter than required to stop the free end 11 at the contact pad 119. It is worth noting that since the inductance is proportional to the loop area which varies quadratically with radius, the percentage error in inductance is twice the percentage error in radius.

This sensitivity to radius error is of concern for several reasons. First, process nonuniformity within the sputter tool will produce some variation in the radius within a wafer and from wafer to wafer. Further variations can occur from run to run. It is highly desired to reduce the sensitivity of the loop area to process variations that cause the actual radius to deviate from the design radius. One way to achieve this is to cause the free end to hit a mechanical stop of some kind. This forces the coil area to depend on physical layout variables rather than process variables. The mechanical stop can take a variety of forms, and provide several levels of constraint.

One simple constraint illustration is provided by the acircular loaded beam. By simply loading a forward segment of the finger 18 (such as by depositing a load layer 13 to a smaller length than shown in FIG. 1), the tip 11 is forced to hit the substrate rather than wrapping inside the coil. The substrate provides a degree of mechanical constraint on the tip 11 since the tip 11 cannot penetrate the substrate. The free end tip 11 can still slide on the surface. To constrain the tip 11 further, a raised stop 25 on the surface of the landing pad can be introduced to prevent the free end from sliding closer than a given distance towards the takeoff point. Further, lateral raised stops 26, 27 (FIG. 12) can be placed to either side of the landing pad to guide the tip 11 and to prevent it from sliding to either side. The edges of the lateral stops 26, 27 can further be tapered in a horn like structure to gather the free end 11 of the finger 18 and funnel it into its desired location. The mechanical stops should not block the entire cross section of the pad available for plating, since this might create a segment of high resistance in the coil. To produce a stop, it is only necessary for the stop to touch a portion of the free end 11 in order to constrain its movement. Tip 11 is shown as tapered to facilitate positioning and final connection to the contact pad.

The stop can be formed from a released elastic member. If formed from a released elastic member, no additional masks are needed to make the stop. A loop formed by such a structure will have a long elastic member and a short elastic member or tab. The long and short elastic members can interlock with each other to constrain their positions. Additionally, the design can provide for the long elastic member touching both the short elastic member and the substrate if desired. Design constraints may be included in the coil such that errors in the fully relaxed radii of the segments do not produce proportionate errors in the coil cross-section. Structures that close until they hit a stop and then stop without fully relaxing have this desired property.

In addition to or in place of a mechanical stop, a tacking operation that adheres the tip 11 in its desired location prior to plating is a useful structure for improving device yield. By tacking the tip 11 in place, it is less likely that the electroplating bath can move the tip 11 before the electroforming operation solidly anchors the tip 11. The tacking can be achieved for example by melting and flowing a small amount of material between the tip and pad, and then hardening it. This would be the natural outcome of designing in a small amount of release window material at the contact point. The reflow operation described above will also tack the tip in place. This can therefore be implemented with no change in cost. The tacking area is intentionally kept small to minimize the contact resistance. The tethers further serve to ensure that the tips that are not fully tacked remain in proximity to the pad. FIG. 11 item 19 shows a strip of release window material that could be used to tack the tip 11 in place.

It is highly desirable to be able to tune the radius of the elastic member 18 after release, especially if the sputter process produces a radius that is not the desired radius. This can be achieved by surrounding the elastic member 18 with additional layers of metal that can be selectively etched away to alter the load on the released elastic member. Each time a layer is removed, the released elastic member will bend by a small amount, allowing the radius to be tuned. When the radius is tuned correctly, the processing can then continue onto the electroforming step. By making the layers thin and/or properly adjusting their stress, the amounts of radius change can be kept small, on the order of a few percent.

No added mask count is needed to implement radius tuning, because the selective nature of the etch defines the start and stop points of the layer removal. Further, no additional materials are needed, since the multilayers utilized can for example consist of the spring and seed metals (e.g. MoCr and Au) already used.

To make radius tuning compatible with plating, it must be ensured that after the radius is tuned, the surface exposes metal that can be plated. In the current industry practice, this means making bilayers of Au and MoCr, and etching down to the next layer of Au.

Figure 14:
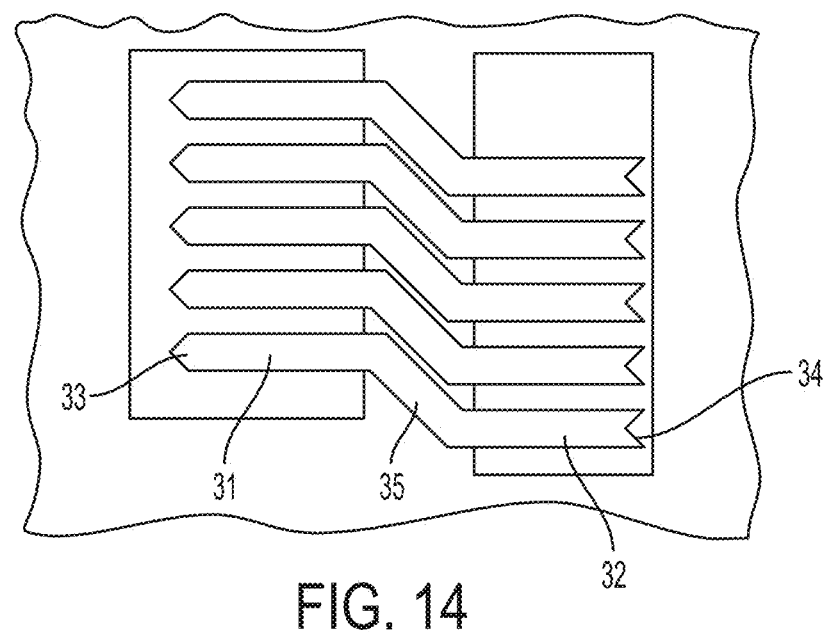
FIG. 14 is a top view of a layout of five mid-air elastic member pairs before release in accordance with some embodiments.
Figure 15:
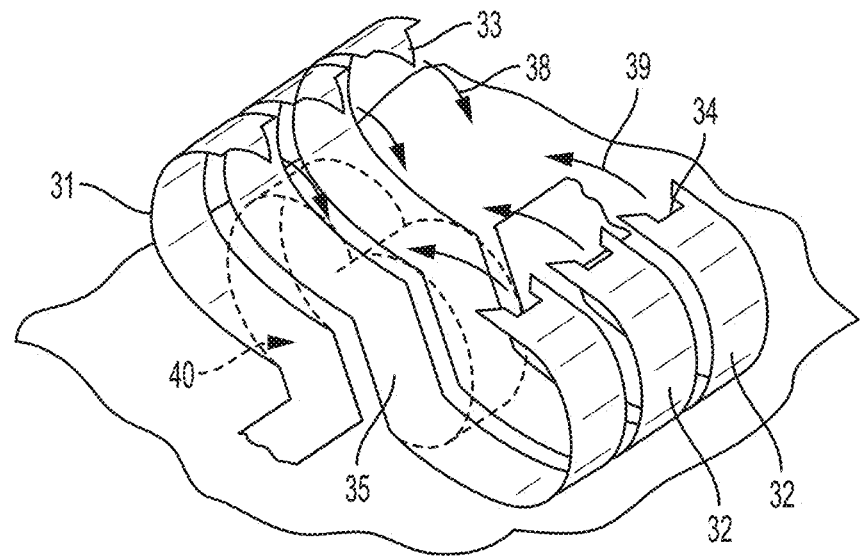
FIG. 15 is a partial perspective view of the member pairs of FIG. 14 during release.

An alternate method of forming an out-of-plane coil structure in which two half loops are closed in mid-air forming a loop winding is shown in FIGS. 14 and 15. The elastic layer is photolithographically patterned into a series of individual elastic members. Each individual elastic member includes a first elastic member 31, a contact portion or bridge for connecting between adjacent loop windings 35 and a second elastic member 32. First elastic member 31 includes an end portion 33 in the shape of an elongated tip and second elastic member 32 includes an end portion 34 having a groove for receiving elongated tip 33. This structure of tips 33 and 34 facilitates catching of the two springs after release so that the two portions may be connected via soldering or plating. The loop winding is formed by removing the release window under each first elastic member and each second elastic member. This can be done at the same time, or sequentially, by using a release material under all the first elastic members different from under all the second elastic members. The first and second elastic members can also be released at different times by placing different perforation densities on them. This causes tip 33 to move in the direction of arrow 38 and tip 34 to move in the direction of arrow 39. When the two tips meet, they are joined at point 40. Pressing and heating causes the solder to reflow and join free end 33 to free end 34.

Figure 17:
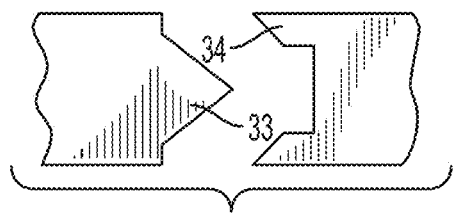
FIGS. 17 and 18 are top views of alternate elastic member tips in accordance with some embodiments.
Figure 18:
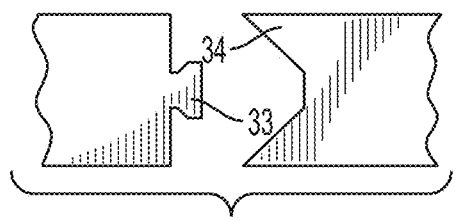

The elongated tips 33 may be, for example shaped as shown in FIG. 17 or FIG. 18. In addition to the shape shown in FIG. 15, end portion 34 may be of the shape shown in FIG. 18. Other variations are possible.

Alternatively, the free ends (without solder) can be connected together by plating. Immersion in a plating bath and depositing metal on accessible metal surfaces both thickens all metal lines and creates bridges between proximal surfaces.

The individual loop halves are shown in FIGS. 14 and 15 as being of approximately the same length. However, the lengths can be varied to aid in the coil formation process. For example, the first elastic members can be made shorter than the second elastic members to ensure that the second elastic members overlap the first elastic members.

Figure 19:
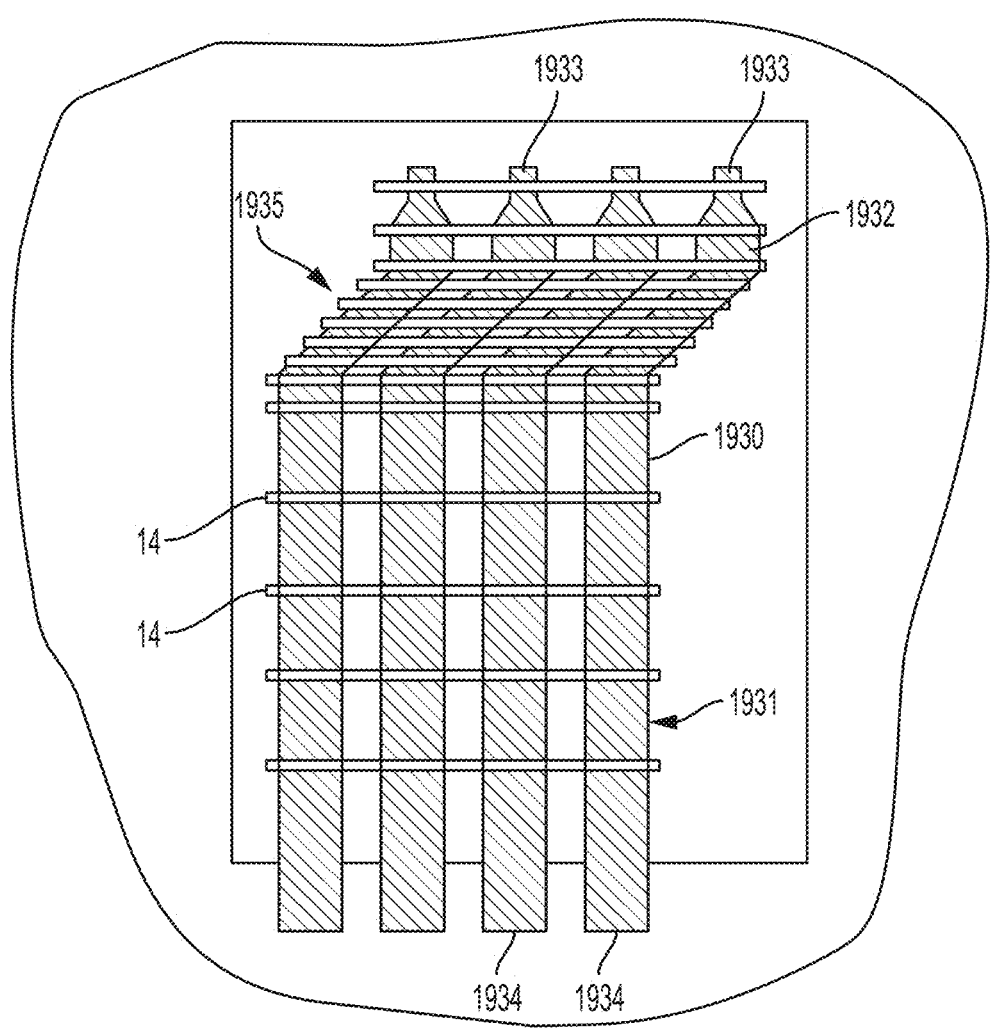
FIG. 19 is a top view of an alternate layout of four elastic members before release in accordance with some embodiments.

An alternative layout for a series of elastic members to be released to form a closed loop structure is shown in FIG. 19. In this embodiment, each elastic member 1930 is patterned into two segments. The first segment 1931 extends from anchor portion 1934 until it reaches second segment 1932. Second segment 1932 is patterned at an angle from first segment 1931 and is terminated by tip portion 1933. A plurality of tethers 14 are added to maintain the spacing between the elastic members 1930. When the release layer is removed, tip 1933 is released followed by second segment 1932 and then segment 1931. When tip 1933 contacts contact 1934 of the adjacent member, the resulting loop is not acircular. The mid-air jog, which occurs where the first and second segments join 1935, allows the free end 1933 to return to the take-off point with an axial offset.

The resistance of the loop closure may be reduced by connecting the free end of a loop back to a contact pad on the substrate with low resistance. Obtaining low resistance at the contact pad requires a good metallurgical junction consisting of highly conducting materials. Coil structures incorporating a solder pad that is reflowed to close the loop achieves a good metallurgical junction as well as low contact resistance. Alternatively, the free end may be joined to the contact pad by plating, either electroless or electroplating. In this method, the loop is formed by releasing the elastic member. The free end comes into either mechanical contact or proximity to a contact pad on the inductor substrate. Then, plating applies conducting material around both the free end and the contact pad, forming a continuous joint between them. In this embodiment, the application of material need not be limited to the free and the pad areas only. Preferably, the plated material has high conductivity, and is plated throughout the loop in order to reduce the coil resistance, thereby beneficially increasing the quality factor.

It is desired from a reliability standpoint to have as wide a pad area as possible in order to accommodate possible axial offsets of the spring ends with respect to their bases. This offset could for example be caused by helical bending due to stress anisotropies, or due to displacement of the fingers due to surface tension forces during wet processing.

Figure 20:
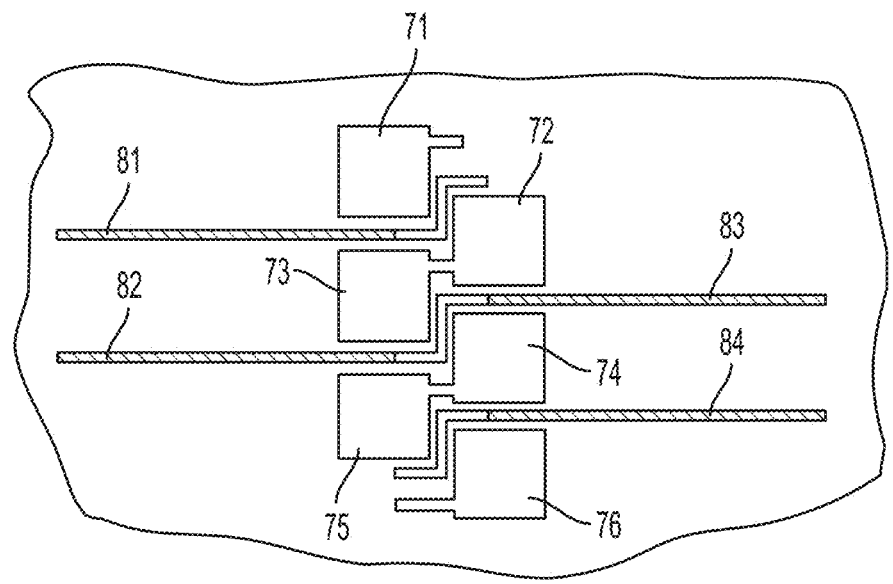
FIGS. 20 and 21 are top views of a bi-directional elastic member layout in accordance with some embodiments.
Figure 21:
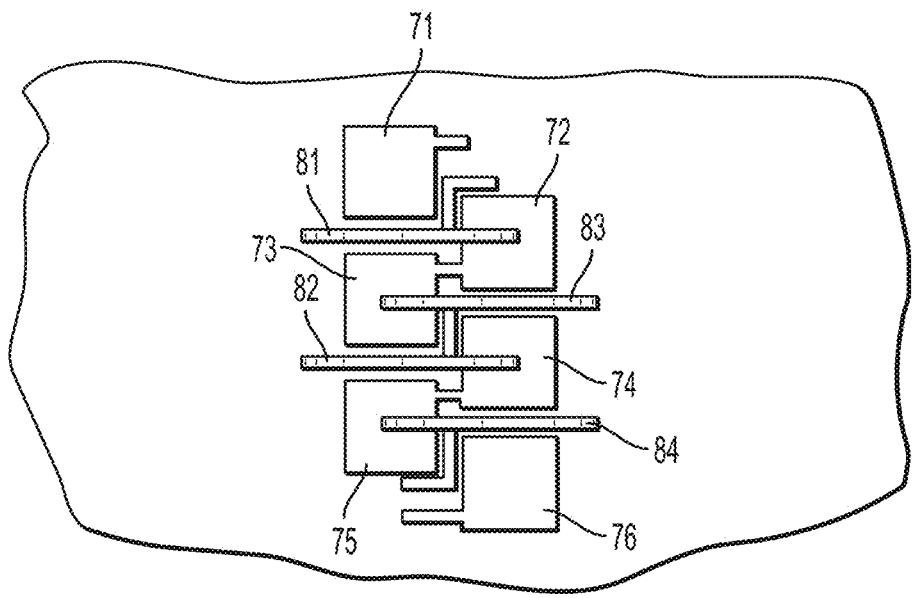

One possible way to extend the pad area is to release elastic members from opposite directions. This also enables the released elastic members to be made wider. FIGS. 20 (before release) and 21 (after release) show a schematic of the layout. In FIG. 20, elastic members 81 and 82 are laid out to release from the left to the right. Elastic members 83 and 84 are laid out to release from right to left. Oversized contact pads 71, 72, 73, 74, 75 and 76 are also shown. This design is advantageous if the undercut can be minimized. A problem may arise in that the release window that opens to allow the springs to lift, will also allow the release etch to advance toward the adjacent pad. Normally, the undercut etch of the release layer is about 30% larger than the undercut needed to release the springs. So, if the undercut needed is 20 microns, the undercut allowed for is about 25 microns. This may be too large in some cases.

A solution to the undercut problem is to clear the conducting release layer between the spring metal traces before applying the release window. This has the drawback that the release layer then cannot be as easily used as a common cathode for electroplating. The technique may work for electroless plating, however the conductance of electroless plated metals is typically lower than what is achievable with electroplating. Conductance has to be kept extremely high in order to meet the quality factor requirements of some applications.

Making the elastic members release from two sides and interleave does not permit the use of tethers since tethers would prevent interleaving. Without tethers, some stiffness and spacing rules may need to be made more conservative in order to prevent entanglement or shorting. Dense toroids designed to lift with their spring tips to the outside and landing pads to the center would not likely be a useful application of the bidirectional springs.

The method of the invention permits process extensions. These process flows are exemplary, but other variations are possible. For example, certain process steps described herein may be combined or eliminated. Layers of solder used to close the loop, could also serve as the release window for the spring release step.

Neural stimulation techniques discussed herein are directed to high-precision spatial targeting of nerve circuits by shaping magnetic fields. The neuromodulation devices disclosed herein provide minimally-invasive and/or feedback-controlled neural modulation for regulating brain stimulation, in particular the visual cortex. The focused magnetic stimulation (FMS) neuromodulation approaches disclosed herein are underpinned by metamaterial coils as discussed above. These micro-engineered metamaterial structures allow for far greater control of electromagnetic fields over conventional transducer technologies. Driven by smart current distribution algorithms, FMS can provide tailored stimulus patterns. The use of an array of metamaterial coils as described above combined with a current distribution algorithm enables complex stimulation patterns.

The use of magnetic stimulation using an array of microcoils as described herein facilitates safely and selectively writing to neurons in the visual cortex. Embodiments disclosed herein use focused magnetic stimulation (FMS), an electromagnetic field manipulation scheme that goes beyond traditional magnetic stimulation, to provide previously unachievable scale, precision, and in vivo adaptability. Using FMS, multiple neurons can be targeted by magnetic beam scanning, beam steering, and beam focusing.

The use of flexible electronics, underpinned by TFT circuitry reduces the amount of inflammation and glial scarring when implanted. The flexible platform also accounts for brain motion. The TFTs can enable logic circuits, multiplexers and shift registers, designed to individually address transducers (sensors and/or stimulators) locally, thereby significantly reducing the number of data lines that need to be routed upstream to the low-power internal electronics module.

Figure 23:
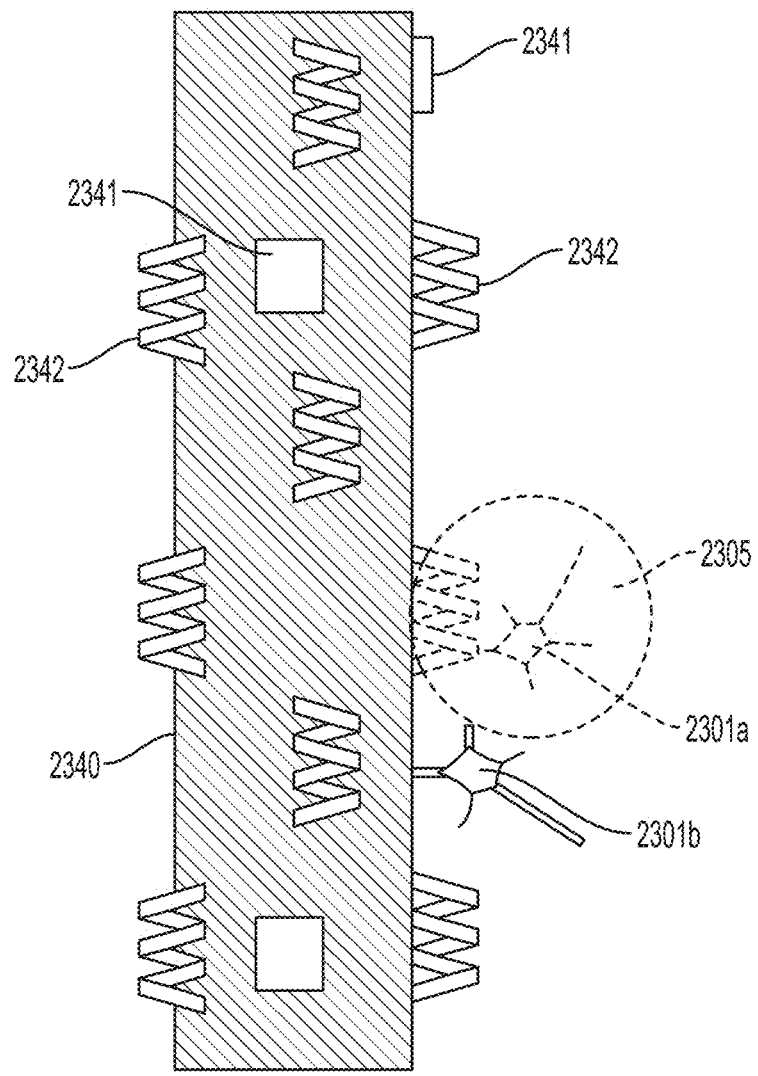
FIG. 23 shows a probe supporting an array of stimulation micro-coils interweaved with an array of neural sensors in accordance with some embodiments.

FIG. 23 shows a probe 2340 supporting an array of stimulation micro-coils 2342 interweaved with an array of neural sensors 2341. The dense pattern of coils 2342 on and/or within the shaft of the probes 2340 can be used to stimulate nearby neurons. Interference effects can be used to steer the field to some degree, but localization away from the immediate vicinity of the probe may be somewhat limited. The core control module ((CCM) 521 shown in FIG. 5) can be configured to control one or more parameters of the current pulses applied to the micro-coils 2342 through the neural stimulation bus 545*a*, including at least amplitude and phase of the current pulses. The current pulses to the coils 2342 may be controlled so the electromagnetic fields produced by the coils 2342 undergo constructive and destructive interference that focuses and/or steers a magnetic flux density to one or more neurons 2301 of interest. The constructive and destructive interference is configured to confine the magnetic flux density produced by the coils 2342 to a focus area 2305 or region of interest within the visual cortex. The focused magnetic flux density causes the one or more neurons of interest 2301*a* to be activated and causes minimal activation of other neurons 2301*b* that are outside the focus area 2305. In some implementations, in addition to the control of the amplitude and phase of the current pulses, the CCM 521 may be configured to control other parameters of the current pulses such as the duty cycle and/or frequency of the current pulses that drive the micro-coils 2342. For example, the current through the coils may be between about 30 to about 70 μA, e.g., about 50 μA. The duration of the current pulse may be about 100 to about 200 μs in some embodiments.

Time-varying electrical currents through the micro-coils generate magnetic fields, which in turn will induce electric fields (Faraday's Law). Like electric stimulation, the induced electric field from the coil will modulate the membrane voltages of nearby neurons, and if strong enough, will lead to their activation (i.e., the generation of action potentials). Magnetic stimulation offers significant enhancements over the state-of-the-art electric stimulation, including but not limited to the following:

(1) the electric fields from magnetic stimulation are highly asymmetric, unlike the electric fields arising from electrodes. This spatial asymmetry is very important because it can be exploited to selectively activate desired neurons, while leaving others quiescent.

(2) The stimulating efficacy of the micro-coils remains constant over time. This is due at least in part to the fact that magnetic fields pass readily through biological substances, and therefore coils remain functional even if they become severely encapsulated due to biological responses to foreign bodies.

(3) There need not be any direct contact between the metal coil and neural tissue, and thus, direct electric currents do not flow into the brain.

Magnetic stimulation by micro-coils is safer and reduces many of the problems that occur at the interface between a stimulating electrode and the brain. In order to keep the neural implant power budget within specified thermal safety limits, it can be helpful to operate the coils at the lowest current possible. In some embodiments, e.g., the vision application described herein, it may be useful to predominantly activate neurons in a single orientation while minimally activating neurons in other orientations or not activating neurons in other orientations.

Figure 24A:
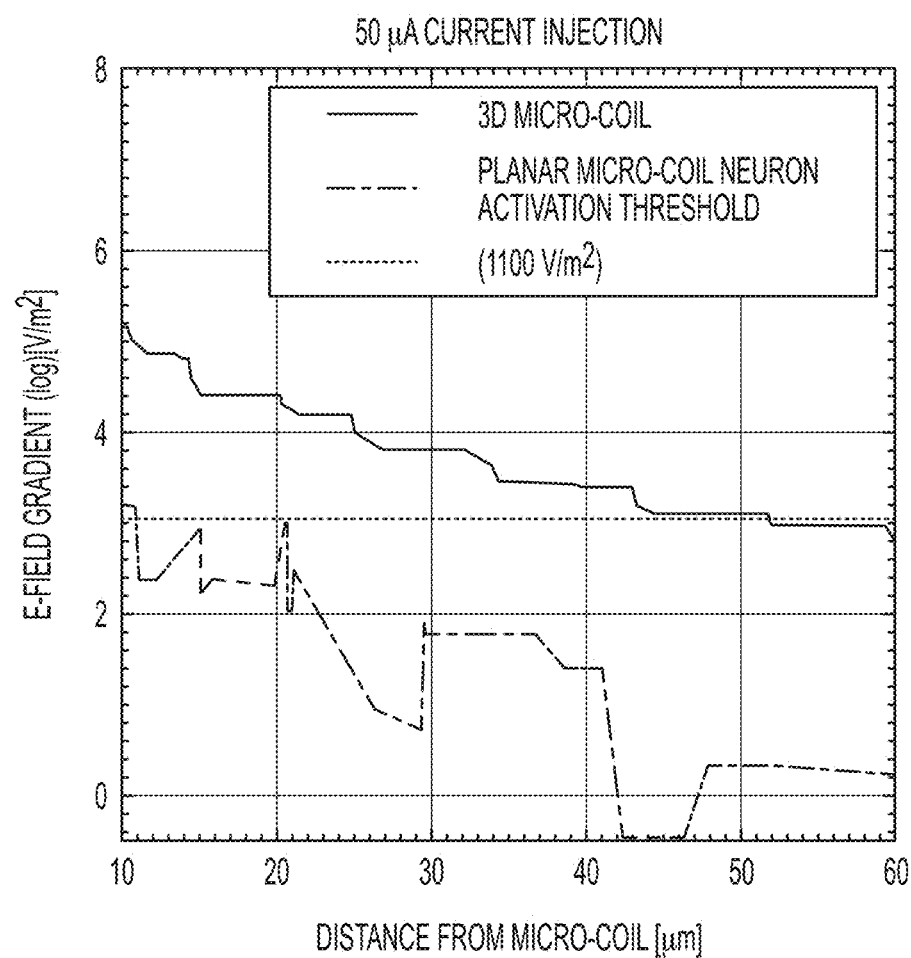
FIG. 24A is a graph showing the electric field gradient (log plot) of 3D coils in accordance with some embodiments vs. an equivalent planar coil.
Figure 24B:
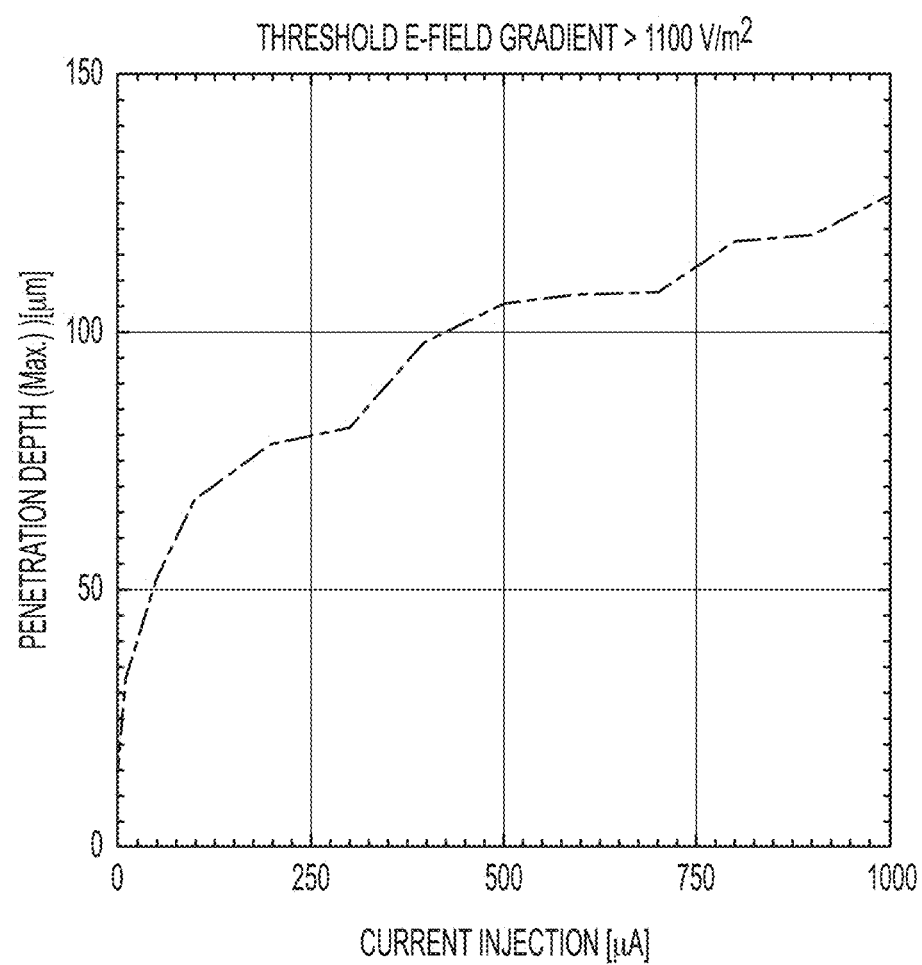
FIG. 24B is a graph showing the penetration depth for a 3D coil as a function of current.

The 3D coils can be configured to satisfy the low current operation, precision and selectivity. Three dimensional micro-coils, such as those described herein, can be configured to yield an order of magnitude larger electric field gradients (the metric for neuron activation) than their planar coil counterparts having similar areal dimensions. FIG. 24A is a graph showing the electric field gradient (log plot) of 3D coils vs. an equivalent planar coil. FIG. 24B is a graph showing the penetration depth for a 3D coil as a function of current. The magnitude of the electric field gradients produced by the 3D micro-coils allow operation of the micro-coils down to about 50 μA as compared to milliamps of current required for planar coils of similar areal dimensions. For example, in some embodiments, the use of the 3D micro-coils in place of planar coils having similar areal dimensions as the 3D micro-coils can reduce the total dissipated power of 100 k coils by about 100 times, e.g., from several Watts to several 10's of milliwatts. As shown in FIG. 24A, for operation at small current, e.g., down to about 50 μA, only the 3D coil is above the activation threshold (1100 V/m$^2$) for neurons. Three dimensional coils have been mass-produced on prefabricated wafers prior to dicing, bonding and packaging. They can also be fabricated on flexible substrates, the approach used for the visual prosthetic system described herein. The resolution of the coils is dependent on their overall dimensions. In some embodiments, the diameter and/or length of the micro-coils may be less than 20 μm which is less than the size of a cortical neuron. Furthermore, unlike planar coils, there are more degrees of freedom to control the direction of stimulation. In 3D coils, the depth of penetration in the tissue is proportional to the size of the coil, but for a fixed coil size, it depends on the magnitude of the injection current as shown in FIG. 24B.

Additionally far greater control over the fields generated by the micro-coils 2342 can be realized using a focused magnetic stimulation (FMS) scheme. In FMS, the magnetic fields are dynamically shaped by using an array of three-dimensional micron scale coils 2342, driven by phase and amplitude-controlled currents. This results in constructive and destructive interference of magnetic fields. Driven by tailored current injections in the coils, FMS enables more localized stimulation in between coils (enhanced focusing), better depth control, and complex stimulation patterns (beamshaping and beamsteering), as compared to current stimulation methods. Tailored stimulations can be obtained with appropriate coil array designs, by selecting the optimal number of elements, array configuration, driving circuits, and current distribution in the coils 2342. Focusing the coils can be achieved by varying drive currents in each coil. Electronic steering can be achieved by modifying the intensity of the currents in each coil 2342 using independent driving circuits.

In some embodiments, the magnetic flux density within the focus region 2305 is greater than about 0.1 Tesla, the electric field strength within the focus region 2305 may be about $Ex=dV/dx>100$ V/m, an electric field gradient within the focus region 2305 may be about $dEx/dx>500$ V/m$^2$ and/or a maximum electric current pulse amplitude in each coil may be less than about 500 mA or even less than about 100 mA. In some implementations, the magnetic flux density, electric field strength and/or electric field gradient produced by the micro-coils 2342 is sufficient to activate one or more neurons 2301*a* within the focus region 2305.

Referring again to FIG. 23, a dense pattern of sensing electrodes 2341 on and/or within the shaft of the probe 2340 can be used to stimulate nearby neurons. Sensing neurons is performed using an array of neural sensors. The neural sensors are interspersed with the neural stimulation coils as shown in FIG. 23. As the action potentials of neurons produce large transmembrane potentials in the vicinity of their somata, these output signals can be measured as a voltage difference by placing sensor electrodes in close proximity to the neurons. To be able to localize single neurons, sensors comprise a compact electrode array (CEA) or tetrodes. A tetrode has four electrically isolated electrodes and the position of the sensed neurons can be estimated by triangulation of the signals picked up by the four electrodes of the tetrode. Triangulation of the signals to determine the neuron position relies on the fact that action potential amplitudes decline as a function of distance between the electrode tip and the neuron. The advantage of using tetrodes, beyond localization, is that they allow a significant reduction in the number of monitoring elements. For example, one tetrode can record about 1000 neurons, within a 300 µm diameter. In order to carry the signals of a large number of sensors over the flexible membrane to the ADC, the sensor signals of the electrical transducers are multiplexed into one signal over a shared data line.

The CCM 521 provides signals to the front end electronics 543a b, c for selection of the column and row of the selected micro-coils 2342 of the probe 2340 through the neural stimulation bus and the neural stimulation control bus.

Figure 25A:
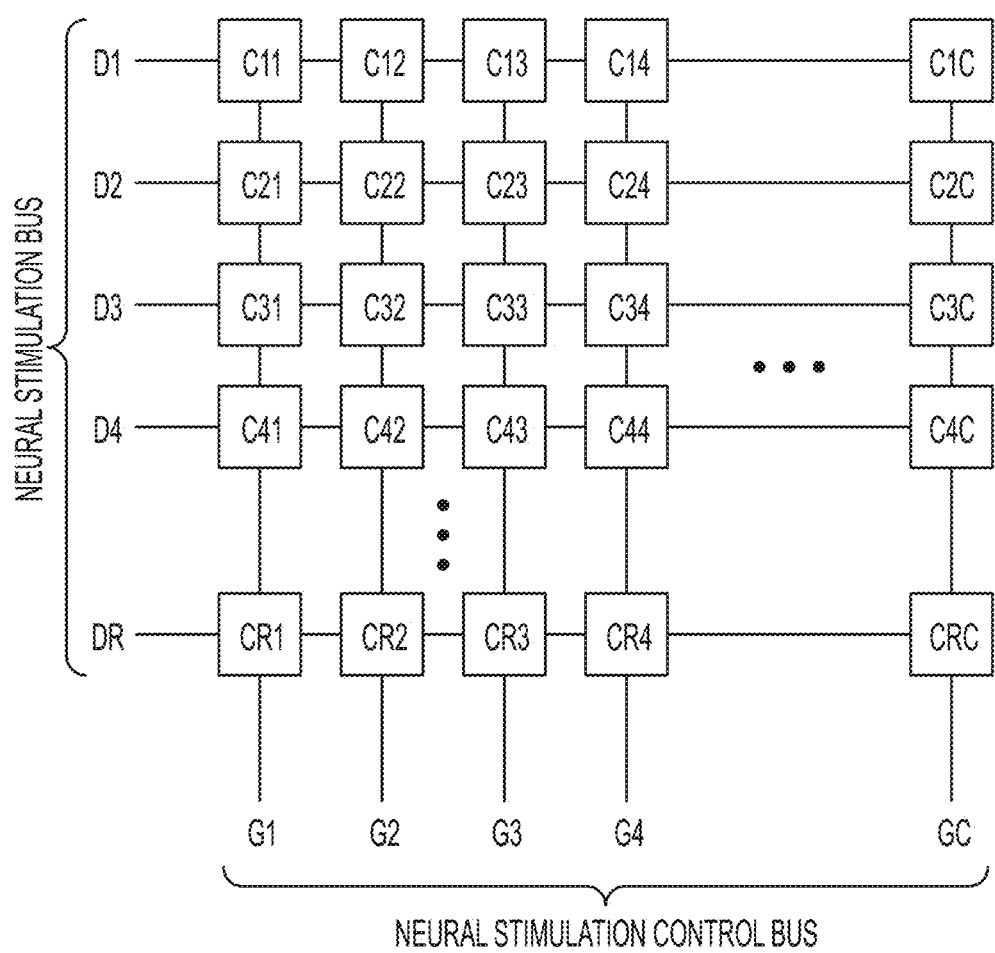
FIG. 25A shows micro-coil addressing in accordance with some embodiments.
Figure 25B:
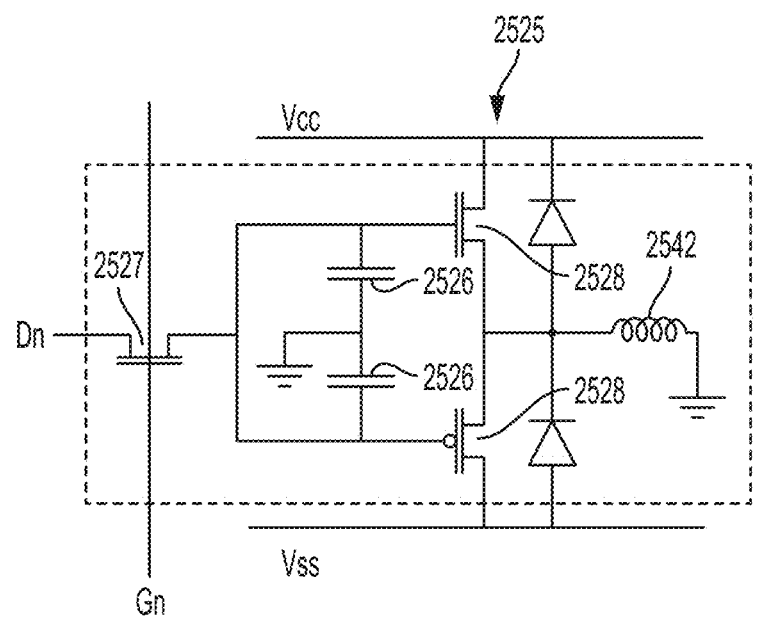
FIG. 25B shows coil driver circuitry configured to drive a micro-coil in accordance with some embodiments.

FIG. 25A is a diagram illustrating row and column addressing through the neural stimulation bus and the neural stimulation control bus for the elements of an micro coil array 2500 C11 through CRC. Each element C11-CRC includes a coil and driver circuitry as shown in FIG. 25B. Each array element C11-CRC is selected by the neural stimulation bus that includes lines D1 through DR and neural stimulation control bus that includes lines G1 through GC. A similar row and column addressing structure can be used for the neural sensors.

Through the neural stimulation bus and the neural stimulation control bus, the CCM 521 provides a predetermined voltage for a coil driver circuitry 2525 shown in FIG. 25B. The value of Dn determines the amplitude of the current pulse(s) delivered to the coil associated with the coil driver circuitry 2525. The timing of the application of Vss and Vcc to a coil driver circuitry 2525 by the CCM 521 determines the phase, duty cycle, and/or frequency of the current pulses provided by the driver circuitry 2525 to the coil 2542.

To program a particular coil 2542, Vcc and Vss are set to zero. A particular column of the micro-coil array is activated by applying a voltage to Gn and a value Dn is applied to the transistor 2527 to set the pulse amplitude value in the gate capacitors 2526 for the coil 2542. The proper bias voltage is set on Dn for the appropriate amount of current that the coil requires, which may be positive or negative.

To activate the coil 2542, Gn and Dn are disabled and Vss and Vcc are applied to the driver circuit 2525 for a duration commensurate with the stimulation parameters. Bipolar operation is enabled by connecting the pair of capacitors 2526 to the complementary pair of transistors 2528.

Figure 26A:
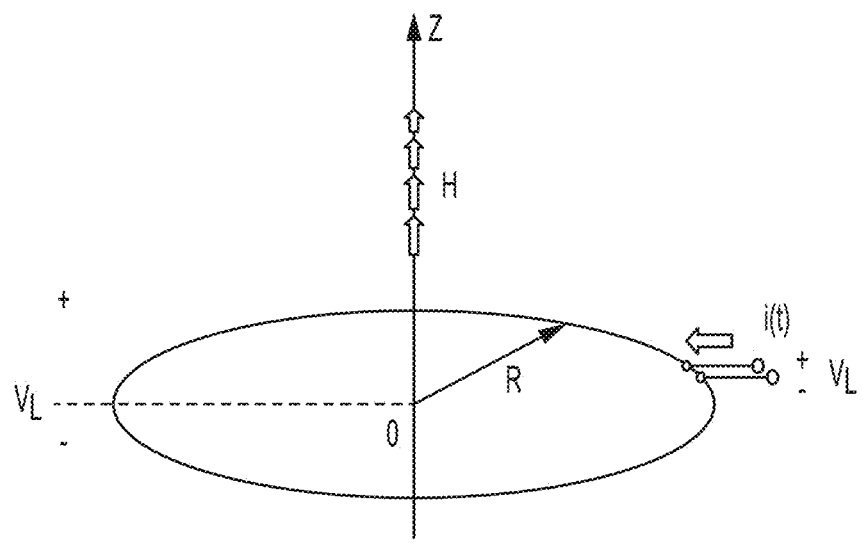
FIG. 26A illustrates the magnetic field created by a single loop coil.

The current pulse through the coil 2542 generates a magnetic field. Referring now to FIG. 26A, which shows a single loop coil, and Equation (1), the magnetic field created by each loop, $H_z^{LOOP}$, increases with the radius of the loop, R, and the intensity of the current, i(t), and decreases with the distance, z, along the axis.

$$H_z^{LOOP}(z) = \frac{\frac{1}{2}R^2 i(t)}{(R^2 + z^2)^{1/2}} \quad (1)$$

Figure 26B:
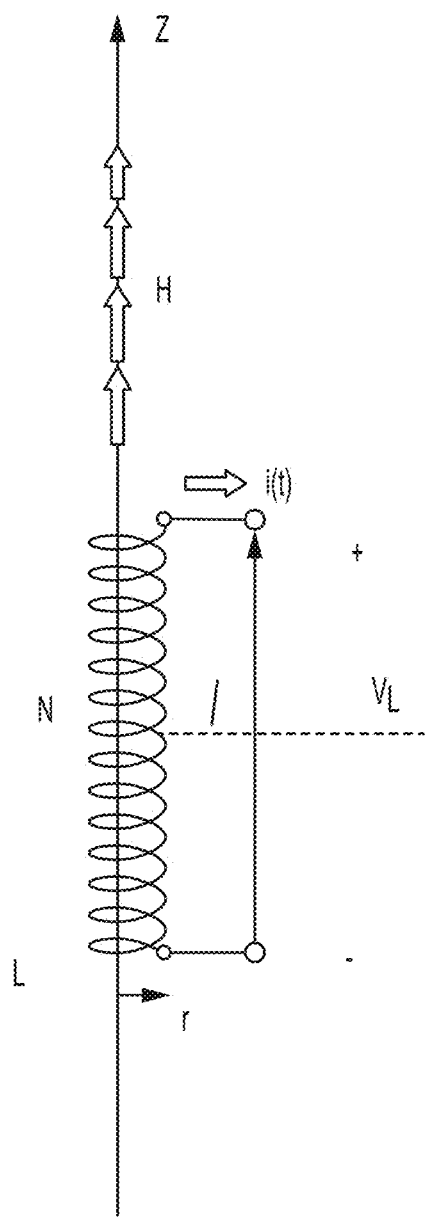
FIG. 26B illustrates the magnetic field created by a multi-loop coil.

The magnetic field of a coil depends on the number of turns, N, the length, l, the pitch, α, and the amplitude of the current as indicated by FIG. 26A, which shows a small radius coil, and Equation (2). By increasing N (or the inductance of the coils), and l, we can considerably increase the resulting magnetic field even for a fixed low current and small radius coil, as deduced from Equation (1). Thus, arranging a large number of small coils in an array configuration, as shown in FIG. 26B will yield an increase in the magnetic field intensity and penetration to specific regions.

$$H_z^{COIL}(z) = \frac{i(t)}{4\pi r \tan\alpha} \left\{ \frac{N\pi r \tan\alpha + z}{\sqrt{r^2 + (N\pi r \tan\alpha + z)^2}} + \frac{N\pi r \tan\alpha - z}{\sqrt{r^2} + \sqrt{r^2 + (N\pi r \tan\alpha - z)^2}} \right\} \quad (2)$$

Figure 27:
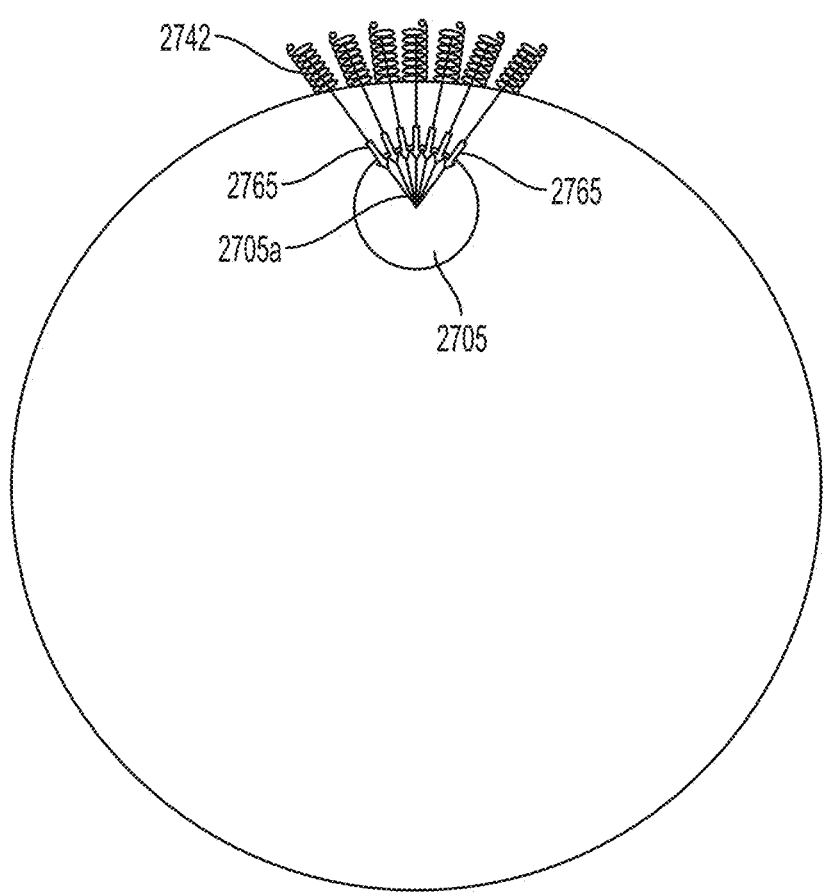
FIG. 27 illustrates manipulation of the field strength of the electric field at a selected location by approximately adding the linear vectors of the individual fields in accordance with some embodiments.

FIG. 27 is a schematic representation of beam focusing and beam steering within a focus region. As illustrated in FIG. 27, since each coil 2742 is driven by a coil current that is independent of other coil currents, it is possible to manipulate the field strength of the electric field at a selected location, such as the focal point 2705a within focus region 2705, by approximately adding the linear vectors 2765 of the individual fields. Thus, tailored stimulations can be obtained with appropriate coil array designs, by selecting the optimal number of elements, array configuration, driving circuits, and current distribution in the coils.

Figure 28A:
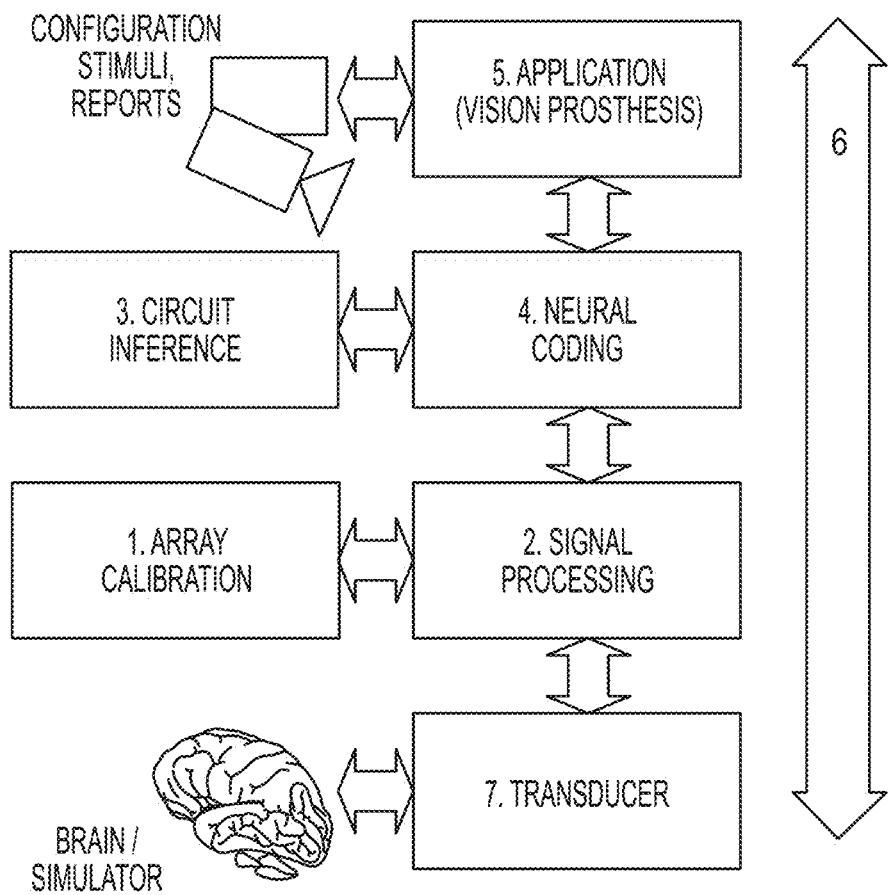
FIG. 28A illustrates an algorithm suite that provides a general neural interface platform that supports the therapeutic vision prosthetic system in accordance with some embodiments.

Embodiments disclosed herein use a suite of algorithms for parallel data processing to convert image signals from the camera into coil stimulation signals. The algorithm suite as illustrated in FIG. 28A provides a general neural interface platform that supports the therapeutic vision prosthetic system.

(1) To enhance accuracy and reduce bandwidth and computation during on-line operation, an offline, off-board array calibration procedure may be employed. The calibration procedure involves determining which neural signal spikes are caused by a particular neuron. The calibration procedure acquires a model by sequentially sampling small neighborhoods of the patient's cortex at high sampling rates (22 kHz) to identify the number, location, type, orientation, firing rate and amplitude distributions of neurons.

(2) The calibration procedure (1) enables an online, on-board signal processing algorithm to perform spike sorting. The information obtained by the calibration procedure is used by the signal processing module to generate coil pulse configuration patterns to stimulate neurons with known registration to those neurons read by spike sorting.

(3) A second offline, off-board procedure infers the circuit structure of the cortex. Circuit inference provides key parameters such as electrode depth relative to cortex surface. Circuit inference may be used on intact animal models to infer relevant features. Algorithms to estimate retinotopic mapping and feature distribution that exploit pattern matching and information theoretic methods can be used.

(4) The information obtained by the circuit inference (2) and the calibration procedure (1) and signal processing (2) is used by the on-line, on-board neural coding algorithm. The neural coding algorithm translates visival stimuli (from the camera) into activation patterns to drive the coil currents in the signal processing layer (2).

(5) The vision prosthetic system includes a user interface that allows therapists to configure the system, monitor performance parameters, and initiate off-board communication to allow calibration and circuit inference.

(6) Authentication, compression and encryption services connect the various modules in the prosthetic system across hardware boundaries.

(7) A simulator can be used to evaluate algorithm design choices, optimize algorithms, and/or provide unit testing.

Figure 28B:
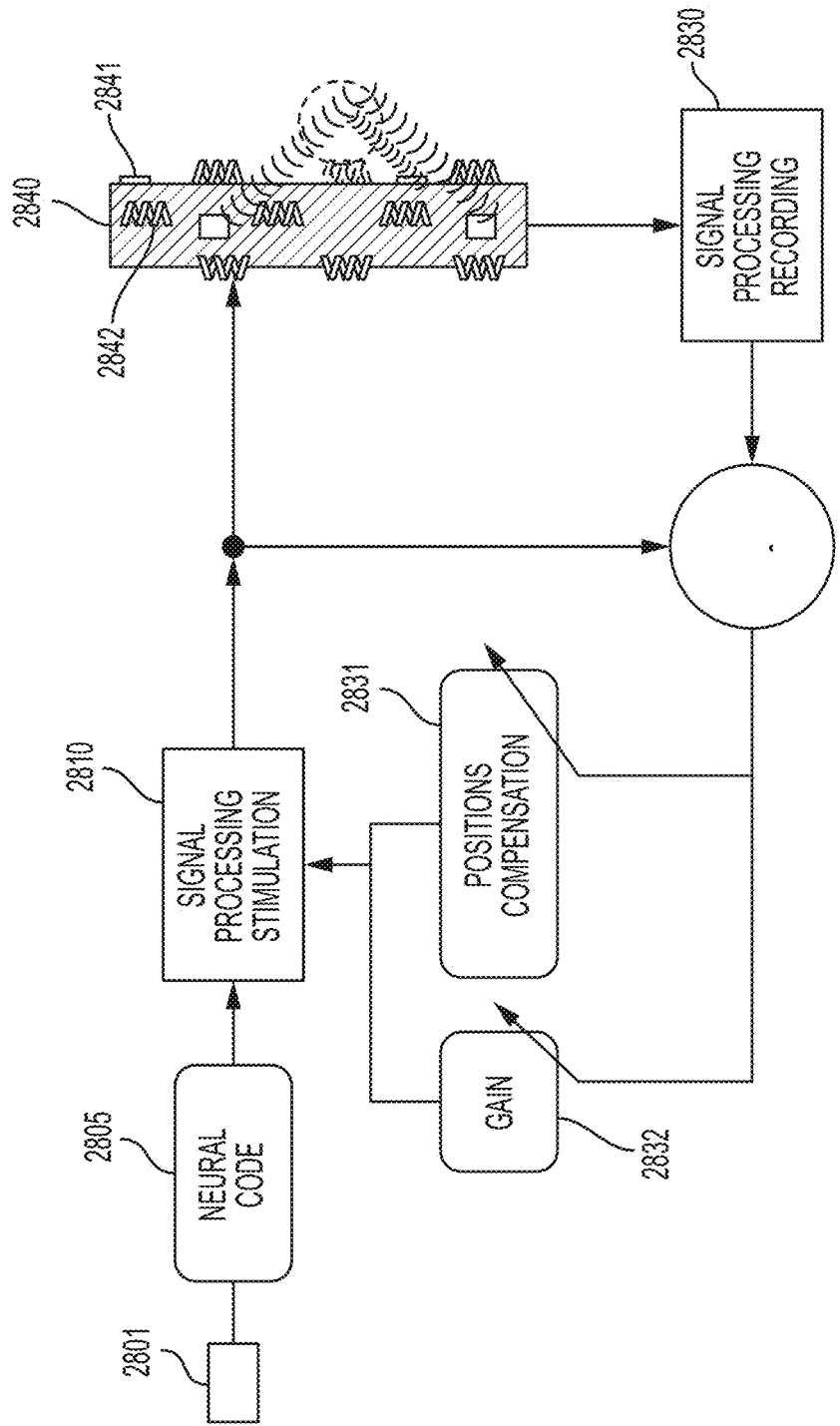
FIG. 28B is a diagram that illustrates methods implemented by the vision prosthetic system to calibrate the neural stimulation so as to simulate vision in a visually impared patient in accordance with some embodiments.

FIG. 28B is a diagram that illustrates methods implemented by the vision prosthetic system to provide neural stimulation so as to simulate vision in a visually impared patient. The process involves first determining the neural code 2805, which is the neural activity within the visual cortex that occurs in response to a particular image, e.g., an image comprising light and dark regions. The neural code 2805 represents the activation of spatially distributed neurons of the visual cortex in response to the image. In addition to the spatially distributed activation of the neurons, the neural code 2805 may also include other parameters of the neural activity, such as the intensity, frequency, phase, etc. of the neural activations.

The neural code initially used for stimulating the neurons of the visual cortex can be derived by high frequency measurement of the neural signals produced by non-human primates with intact vision pathways at the intended stimulation areas and/or optionally other areas of the visual pathway. Utilizing neural coding obtained from non-human primates with intact vision pathways isolates the challenge of synthesizing enough features to provide high quality information to the cortex from the challenge of determining existing wiring in blind animal models. Neuron-level recording allows capture of neuron-level sensed data without knowing the specific wiring of signals in the non-human primate subjects.

After the neural code is determined, it is then mapped to a stimulation pattern of the visual cortex. The stimulation pattern comprises the stimulation signals that selectively activate the micro-coils of the probe. The stimulation pattern may involve the number and position of the micro-coils that are activated as well as the frequency, amplitude, phase, etc. of the stimulation signals that activate the micro-coils. The stimulation pattern is determined in conjunction with a calibration process that determines which neural signal spikes are caused by a particular neuron.

Camera signals from the camera 2801 correspond to a particular image component. The neural encoder for the image component translates the camera signals into a neural stimulation pattern that corresponds to the image component. The visual prosthetic system applies the stimulation signals 2810 to the micro-coil stimulators 2842 of the probes 2840 according to the stimulation pattern that is intended to produce the neural code 2805 associated with the image component. For enhanced visual restoration, the stimulation pattern may need to be adapted for the particular patient. The neural sensor signals are obtained 2830 from the neural sensors 2841 and the sensor signals are used to provide a feedback signal. The initial stimulation mapping is subsequently refined using the feedback signal to be a patient-specific mapping using machine learning. The machine learning is implemented and the stimulation mapping is updated accordingly until the stimulation from the micro-coils produces the neural signals that correspond to the image component. Adaptation of the stimulation pattern may involve adapting one or both of the positions 2831 of the micro-coils activated and/or gains 2832 of the stimulation signals applied to the micro-coils and/or other parameters of the stimulation. The adapted stimulation pattern can be stored for future use in conjunction with the particular image component.

The embodiments discussed herein can be implemented using a patient-internal device having a volume of about 0.8 cm$^3$ capable of operating with less than about a 0.6° C. rise in tissue temperature. The number of write channels may be between about 512 and/or the number of read channels may be between about 256. The latency of the channels, e.g., the waiting time between the order to read/write to a neuron in the region of interest and the beginning of the data-read/write operation, can be in a range of about 20 ms to about 7 ms. Isolation between the channels can be between about 30 dB to about 70 dB. The region of interest which can be sensed and/or stimulated by the neural probe may be an area about 0.16 cm$^2$ to about 2 cm$^2$ of the visual cortex. The region of interest can be stimulated with a resolution between about 40 μm to about 20 μm.

The communication channel may have a bandwidth of about 100-500 Mbps; a power budget of between about 700 mW to about 120 mW; a link budget of between about 35 to about 40 dB. The communication channel may use run length encoding with 2:1 or 4:1 compression in some implementations.

The foregoing description of various embodiments has been presented for the purposes of illustration and description and not limitation. The embodiments disclosed are not intended to be exhaustive or to limit the possible implementations to the embodiments disclosed. Many modifications and variations are possible in light of the above teaching.

The invention claimed is:

1. An implantable subsystem comprising:
multiple implantable neural probes disposed on a flexible substrate, each neural probe configured to magnetically stimulate brain neurons, each probe comprising:
an array of magnetic neural stimulators configured to magnetically stimulate neurons; and
neural probe activation circuitry comprising thin film switches disposed on the flexible substrate, the thin film switches electrically coupled to row and column activation lines and configured to selectively activate the magnetic neural stimulators of the array in response to neural stimulation activation signals carried on the activation lines.

2. The subsystem of claim 1, each neural probe further comprising:
an array of electrical neural sensors disposed on the flexible substrate and interleaved with the magnetic neural stimulators, the neural sensors configured to electrically sense the brain neurons; and
the thin film switches configured to selectively activate the neural sensors of the array in response to neural sensor activation signals carried on the activation lines.

3. The subsystem of claim 1, wherein each probe has a three dimensional shape such that an exterior surface of the probe comprises at least a portion of a first surface of the flexible substrate and an interior surface of the probe comprises at least a portion of a second surface of the flexible substrate.

4. The subsystem of claim 3, wherein the three dimensional shape is a cylinder.

5. The subsystem of claim 4, wherein each cylinder has a diameter of about 30 to about 100 μm and a length of about 1.4 to about 2 mm.

6. The subsystem of claim 4, wherein:
each probe comprises a probe area of the flexible substrate; and
the flexible substrate is a multi-layered stress-engineered structure at least in the probe area.

7. The subsystem of claim 6, wherein a bridge of the flexible substrate attaches each probe area to other areas of the flexible substrate.

8. The subsystem of claim 7, wherein each probe is disposed at an angle to the other areas of the flexible substrate at the bridge.

9. The subsystem of claim 2, wherein the electrical neural sensors are disposed on an exterior surface of the probe and the neural probe activation circuitry is disposed on an interior surface of the probe.

10. The subsystem of claim 1, wherein the magnetic neural stimulators have a stimulation resolution between about 15 to about 25 μm.

11. The subsystem of claim 1, wherein the magnetic neural stimulators comprise three dimensional coils.

12. The subsystem of claim 11, wherein each of the three dimensional coils have a length and diameter of about 10 μm to about 30 μm.

13. The system of claim 11, wherein the three dimensional coils have a stress gradient that causes loops of the coils to curl out of plane.

14. The subsystem of claim 1, wherein:
the flexible substrate has a distal region, a proximal region, and a center region extending between the distal region and the proximal region; and
the multiple neural probes are disposed at the distal region of the flexible substrate; and
further comprising an interface area disposed at the proximal region of the flexible substrate and configured to be electrically and mechanically coupled to an implantable device configured to control operation of the neural probes.

15. The subsystem of claim 1, wherein the neural probes are configured to penetrate into the brain.

16. The subsystem of claim 11, wherein the neural probes are configured to penetrate into the visual cortex to at least the $5^{th}$ cortical layer.

17. An implantable subsystem, comprising:
a flexible substrate having a first surface and a second surface, the flexible substrate having a distal section, a proximal section, and a center section extending between the distal section and the proximal section;
a two dimensional array of neural probes disposed at the distal section of the flexible substrate, the neural probes configured to stimulate and sense neurons, each neural probe comprising:
a probe area of the flexible substrate and having a three dimensional shape with an external surface comprising at least a portion of the first surface of the flexible substrate and an internal surface comprising at least a portion of the second surface of the probe;
an array of magnetic neural stimulators configured to magnetically stimulate neurons;
an array of neural sensors disposed on the external surface of the probe and configured to electrically sense the neurons; and
probe addressing circuitry comprising thin film switches configured to selectively activate the magnetic neural stimulators and the neural sensors, the probe addressing circuitry disposed on the internal surface of the probe; and
an interface region disposed at the proximal section of the flexible substrate and configured to electrically and mechanically couple to an implantable device that controls operation of the neural probes via the probe addressing circuitry.

18. The subsystem of claim 17, wherein the magnetic neural stimulators comprise three dimensional coils.

19. The subsystem of claim 18, wherein each of the three dimensional coils have a length and diameter of about 15 μm to about 25 μm.

20. The subsystem of claim 19, wherein, when laid flat, each probe area of the flexible substrate has a surface area of about 0.0048 cm$^2$ to about 0.032 cm$^2$ and contains about 250 to about 450 of said three dimensional coils.

* * * * *